United States Patent [19]

Otsu et al.

[11] Patent Number: 5,582,817
[45] Date of Patent: Dec. 10, 1996

[54] REMEDY FOR DERMATOPATHY AND METALLOTHIONEIN INDUCER

[75] Inventors: Yoshiro Otsu, Minoo; Yaeno Arima, Kobe; Katsuyuki Nakajima, Maebashi; Masakazu Adachi, Takasaki; Tsutomu Muramatsu, Nara; Katsumi Hanada, Hirosaki, all of Japan

[73] Assignees: Otsuka Pharmaceutical Co., Ltd., Tokyo; Japan Immunoresearch Laboratories Co., Ltd., Gunma, both of Japan

[21] Appl. No.: 122,585

[22] PCT Filed: Feb. 3, 1993

[86] PCT No.: PCT/JP93/00130

§ 371 Date: Oct. 4, 1993

§ 102(e) Date: Oct. 4, 1993

[87] PCT Pub. No.: WO93/14748

PCT Pub. Date: Aug. 5, 1993

[30]  Foreign Application Priority Data

Feb. 3, 1992  [JP]  Japan ............... 4-017612
  May 6, 1992  [JP]  Japan ............... 4-113633
  Dec. 4, 1992  [JP]  Japan ............... 4-325633
  Dec. 28, 1992  [JP]  Japan ............... 4-348618

[51] Int. Cl.$^6$ ............ A61K 7/42; A61K 31/555; A61K 31/315

[52] U.S. Cl. ............ 424/59; 514/188; 514/494; 546/5

[58] Field of Search ............... 546/5; 424/59

[56]  References Cited

U.S. PATENT DOCUMENTS 3,189,630  6/1965  Smutny ............... 546/5
3,879,396  4/1975  Ramey et al. ............... 546/5
4,089,842  5/1978  Ramey et al. ............... 546/5

OTHER PUBLICATIONS

Chemical Abstracts, vol. 96:148984, Abstract of JP. Kokai 5614 7705, Nov. 16, 1981.

Chemical Abstracts, vol. 96:148983, Abstract of JP Kokai 56147704, Nov. 16, 1981.

Chemical Abstracts, vol. 94:162604 Abstract of JPn. Kokai, 56008309, Jan. 28, 1981, (Fukuda).

Primary Examiner—Shelley A. Dodson
Attorney, Agent, or Firm—Sughrue, Mion, Zinn, Macpeak & Seas

[57]  ABSTRACT

Zinc salts, zinc complexes or salts thereof of a compound selected from the group consisting of nicotinamides, picolinamides, 3,4-dihydroxybenzoic acids, amino acids, peptides, hinokitiols and pyridine carboxylic acids represented by formula (1):

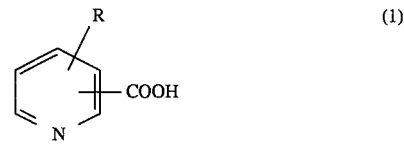

possess a metallothionein inducing effect, effect of suppressing the production of sunburn cells, and therefore, useful as cosmetics and as drugs which are for ameliorating sunburn, preventing sunburn, ameliorating skin diseases, relieving irradiation disorders, and the like.

58 Claims, 3 Drawing Sheets

REMEDY FOR DERMATOPATHY AND METALLOTHIONEIN INDUCER

TECHNICAL FIELD

The present invention relates to a method of suppressing the production of sunburn cells which is applicable in various manners with minimal adverse side effects, a method of inducing metallothionein, a method of treating skin diseases and a method of screening ultraviolet rays, and further relates to cosmetic compositions and UV screening compositions.

BACKGROUND ART

Conventionally, steroids and zinc oxide formulations have been topically used as medicines for treating skin diseases such as dermatitis, sunburn, neurodermatitis, eczema and anogenital pruritus. Steroids, however, have been difficult to administer in large quantities for a prolonged period due to their strong adverse side effects. Zinc oxide formulations, which have local astringent action, involve problems with respect to the manufacture of pharmaceuticals, since they are insoluble in water and are not usually administered internally.

In the meantime, developments in atomic energy have revolutionized many fields such as power generation, diagnoses of various diseases, and radiation therapy for the treatment of cancer. Radiotherapy, especially, raises a problem of side effects associated with radiation damage. These effects include early stage problems such as a decrease in the number of leukocytes, loss of hair and the flushing of skin, and late stage problems which may only be recognized after a long period of time, such as cartinogenesis, cataracts and fetal disorders. There are also systemic disorders due to acute exposure to radiation, for example, radiation sickness caused by atomic weapons and accidents in atomic power stations. Symptoms of nausea, anorexia, and a general weariness similar to a hangover are known as adverse side effects of radiation therapy ["Active Oxygen", Tsutomu KAGIYA, 334–360, published by Ishiyaku Shuppan K. K., 1987]. One of the causes of the above disorders is said to be an abnormal production of free radicals in the body due to exposure to radiation. However, as yet there have not been effective medicines for preventing these disorders or otherwise minimizing the effects of exposure to radiation.

On the other hand, in the field of cosmetic compositions, UV absorbers such as para-aminobenzoic acid derivatives, cinnamic acid derivatives, salicylic acid derivatives, camphor derivatives, urocanic acid derivatives, benzophenone derivatives and heterocyclic derivatives are incorporated into compositions exclusively for external use and used for purposes of preventing sunburn or the like. These UV absorbers suppress the formation of erythema of the skin and bulla, and are also employed for the purposes of preventing pigmentation by suppressing the formation of melanin and thereby preventing the aging of the skin.

There are two different types of dermatological reactions caused by sunlight, one is an acute inflammatory change in the skin called sunburn, and the other is a subsequent melanin pigmentation called suntan. The light having a wave length in the range of 320 nm or less, called UVB, induces sunburn and is responsible for erythematous change. The erythemic reaction caused by UV rays, as opposed to a burn injury, does not occur immediately after the exposure to the sunlight, but rather occurs after a latent period of several hours. When sunburned skin is histopathologically examined, various degrees of inflammatory changes are recognized in the epidermis and dermis depending on the dose of radiation. Among such changes, a notable one is the generation of so-called sunburn cells (SBC) in the epidermis. A histologically stained tissue sample presents strongly and acidophilically stained cells which have pyknotic nuclei. This phenomenon indicates the necrosis of epidermal cells ["Fragrance Journal", 9, 15–20 (1991)]. In order to prevent sunburn, para-aminobenzoic acid derivatives, cinnamic acid derivatives or the like UV absorbers mentioned above are used, but their UV absorbing effects are not necessarily satisfactory. What is more, they raise problems of cumbersome handling upon use, poor stability, low compatibility with other components of the composition, and also involve unsolved problems in water-resistance and oil-resistance.

In the field of medicines for the treatment of skin diseases, development of medicines which have minimal adverse side effects, and which have novel functions obtainable by both external and internal administrations has been desired. Also, in the field of the therapy and prevention of radiation disorders, medicines which can suppress and cure the disorders caused by oxidative reactions have been desired. Fastly, in the field of the manufacture of cosmetics, cosmetics which overcome the above-mentioned problems such as handling upon use and stability of the composition have been desired. Accordingly, the present invention is to provide therapeutic agents for treating skin diseases having the above-mentioned characteristics, induction of metallothionein, for suppressing the formation of sunburn cells, and for use in cosmetic compositions.

Zinc, one of the indispensable trace metals in the living body, is known to participate in the development of sexual organs, promotion of wound healing and is also known to be a component of a metalloenzyme, an accelerator for dehydrogenase, and to have various functions such as activating the immune system. Zinc is further known to be an inducing factor of metallothionein (MT), a metal-combining protein. It is reported that MT functions as a scavenger of free radicals which are generated at the onset of inflammations ["Dermatologica", Hanada, k., et al., 179 (suppl. 1) 143 (1989)].

The present inventors considered that, in dermatological inflammations caused by external irritative stimulants, such as sunburn or the like, MT could act to quench the free radicals released from leukocytes, especially granulocytes which gather at the inflamed region, and thereby exhibit an anti-oxidation action to diminish cell damage, especially to normal lymphocytes, to activate the immune system and further to prevent the accelerated aging of the skin. They further considered that the formation of sunburn cells (SBCs) could be suppressed by administering zinc for inducing MT to be present, or to increase MT in the epidermal keratinous layer. They furthermore considered that MT's anti-oxidation action can also be useful in the treatment of skin problems resulting from radiation therapy by X rays, alpha rays, beta rays, gamma rays, neutron rays and accelerated electron rays.

In the above situation, the present inventors have studied various zinc compounds with respect to their pharmacological activities, and have found that zinc salts or zinc complexes of a certain compound have an unexpected and excellent action of inducing MT and suppressing SBC production due to UV rays, and thereby useful as components of cosmetic compositions or medicines for purposes of ameliorating sunburn, preventing sunburn, ameliorating sufferings from skin diseases and ameliorating other radiation induced disorders, leading to completion of the invention.

DISCLOSURE OF THE INVENTION

The present invention provides a method of suppressing the production of sunburn cells, a method of inducing metallothionein, a method of treating skin diseases and a method of screening UV rays, all of which are achieved by administering an effective amount of a composition comprising a zinc salt, zinc complex or a salt thereof of a compound selected from the group consisting of nicotinamide, picolinamide, 3,4-dihydroxybenzoic acid, amino acids, peptides, hinokitiol and pyridine carboxylic acid which are represented by the following formula (1):

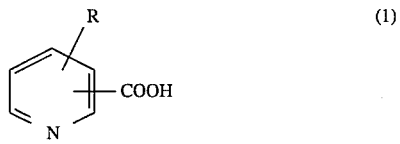

(1)

[wherein R represents hydrogen, hydroxy, nitro, halogen, alkoxy, alkyl, carboxy, —COOM (M represents an alkali metal) or an oxide on a nitrogen atom], The present invention also provides a cosmetic composition, and especially a cosmetic composition for screening UV rays, which comprises the mentioned zinc salt, zinc complex or a salt of the complex.

BEST MODE FOR IMPLEMENTING THE INVENTION

Figure 1:
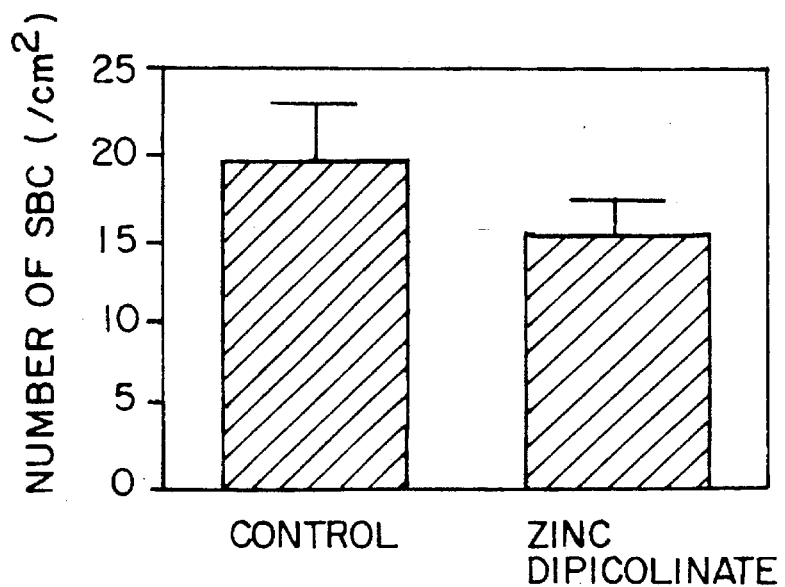
FIG. 1 is a graph which shows the number of SBC per 1 cm formed in the epidermis as a result of UV ray irradiation.

In the present invention, illustrative halogen atoms represented by R in formula (1) described above include chlorine, fluorine, bromine and iodine. Examples of alkoxy groups include C1 to C12 linear or branched alkoxy groups such as methoxy, ethoxy, n-propoxy, isopropoxy, n-butoxy, tert-butoxy, n-pentyloxy, n-hexyloxy, n-heptyloxy, n-octyloxy, 2-ethylhexyloxy, n-nonyloxy, n-decyloxy, n-undecyloxy and n-dodecyloxy. Examples of alkyl groups include C1 to C12 linear or branched alkyl groups such as methyl, ethyl, n-propyl, isopropyl, n-butyl, tert-butyl, n-pentyl, n-hexyl, n-heptyl, n-octyl, n-nonyl, n-decyl, n-undecyl and n-dodecyl.

Zinc salts or zinc complexes of the compound represented by formula (1) include zinc dipicolinate, zinc salts or zinc complexes of 2,5-pyridine dicarboxylic acid, bis(2,5-pyridine dicarboxylate)zinc.2Na or bis(2,5-pyridine dicarboxylato)zinc.2Na, zinc salts or zinc complexes of 2,6-pyridine dicarboxylic acid, zinc salts or zinc complexes of 3-pyridine carboxylic acid, zinc salts or zinc complexes of 4-pyridine carboxylic acid, zinc salts or zinc complexes of 2,4-dicarboxypyridine, zinc salts or zinc complexes of 3-hydroxy-2-carboxypyridine, zinc salts or zinc complexes of 3-n-propoxy-2-carboxypyridine, zinc salts or zinc complexes of 3-n-hexyloxy-2-carboxypyridine, zinc salts or zinc complexes of 5-n-propoxy-2-carboxypyridine, zinc salts or zinc complexes of 5-n-butoxy-2-carboxypyridine, zinc salts or zinc complexes of 5-(2-ethyl-hexyloxy)-2-carboxypyridine, zinc salts or zinc complexes of 6-n-butoxy-2-carboxypyridine, zinc salts or zinc complexes of 3-methoxy-2-carboxypyridine, zinc salts or zinc complexes of 5-methoxy-2-carboxypyridine, zinc salts or zinc complexes of 6-methoxy-2-carboxypyridine, zinc salts or zinc complexes of 6-n-hexyloxy-2-carboxypyridine, zinc salts or zinc complexes of 3-methyl-2-carboxypyridine, zinc salts or zinc complexes of 4-methyl-2-carboxypyridine, zinc salts or zinc complexes of 4-tert-butyl-2-carboxypyridine, zinc salts or zinc complexes of 5-methyl-2-carboxypyridine, zinc salts or zinc complexes of 5-n-hexyl-2-carboxypyridine, zinc salts or zinc complexes of 3-n-undecyl-2-carboxypyridine, zinc salts or zinc complexes of 4-n-undecyl-2-carboxypyridine, zinc salts or zinc complexes of 5-n-butyl-2-carboxypyridine, zinc salts or zinc complexes of 6-n-undecyl-2-carboxypyridine, zinc salts or zinc complexes of 4-nitro-2-carboxypyridine, zinc salts or zinc complexes of 4-chloro-2-carboxypyridine, zinc salts or zinc complexes of 5-hydroxy-2-carboxypyridine, zinc salts or zinc complexes of 4-bromo-2-carboxypyridine, zinc salts or zinc complexes of 4-fluoro-2-carboxypyridine, zinc salts or zinc complexes of 6-chloro-2-carboxypyridine and zinc salts or zinc complexes of 2-carboxypyridine-N-oxide.

No particular limitation is imposed on amino acids useful in the present invention, and any neutral amino acids, basic amino acids and acidic amino acids may be used as long as they can form a salt or a complex together with zinc. Examples of such amino acids include glycine, alanine such as α-alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine. They may be in any form of D, L or DL. As for peptides, mention may be given to those of natural origin and synthetic peptides, with preferable peptides being those having a molecular weight of 3000 or less in view of the oral route or percutaneous absorption. Examples of the peptides include oligopeptides containing 2 to 10 amino acids such as dipeptides, tripeptides, tetrapeptides, pentapeptides, hexapeptides, heptapeptides, octapeptides, nonapeptides and decapeptides which are combinations of identical or different amino acids mentioned hereinabove. The amino acids which are the constituents of these peptides may be a single amino acid or any combinations of 2 or more amino acids. In detail, illustrative examples include oligopeptides which are constituted by histidine and the above-mentioned amino acids, di L-arginine-L-aspartic acid, L-arginine-L-glutamic acid, glycylglycine, L-glutamic acid-DL-alanine, di DL-pyrrolidone carboxylic acid, L-alanyl-glycyl-glycine, β-alanyl-L-histidine, glycyl-glycyl-glycine, glycyl-glycyl-glycyl-glycine, L-leucyl-glycyl-glycine, DL-leucyl-glycyl-DL-phenylalanine and glutathione.

Among the zinc salts or zinc complexes useful in the present invention, those having a basic group can be easily converted to acid addition salts thereof by having them react with general acids which are pharmaceutically or cosmeticologically accepted. Examples of these acids include inorganic acids such as sulfuric acid, phosphoric acid and hydrobromic acid, and organic acids such as oxalic acid, acetic acid, succinic acid, malonic acid, methanesulfonic acid, maleic acid, fumaric acid, malic acid, tartaric acid, citric acid and benzoic acid.

Among the zinc salts and zinc complexes useful in the present invention, those having an acidic group can be easily converted to salts by having them react with general basic compounds which are pharmaceutically or cosmeticologically accepted. Examples of these basic compounds include NaOH, Ca(OH)$_2$, Na$_2$CO$_3$ and KHCO$_3$.

The zinc compounds useful in the present invention encompass optical isomers and stereochemical isomers.

The zinc compounds useful in the present invention include both known compounds and novel compounds. They are prepared by or according to known methods. In each step of the process, the target compound can be readily isolated and purified by routine means of separation. As to such separating means, mention may be given to solvent extraction, dilution, recrystallization, column chromatography, preparative thin layer chromatography and the like.

The zinc compounds useful in the present invention can be prepared by reacting a compound represented by formula (1), namely, pyridinecarboxylic acids, nicotinamides, picolinamides, 3,4-dihydroxy benzoic acids, amino acids, peptides or hinokitiols, with an ordinary zinc salt [II] in a suitable inert solvent.

No particular limitation is imposed on the zinc salt [II], and ordinary zinc salts can be used. Illustrative examples of the zinc salt include zinc salts of lower alkane acids such as zinc salts of acetic acid and zinc salts of propionic acid; zinc salts with inorganic acids such as zinc sulfate, zinc nitrate, zinc chloride, zinc bromide, zinc iodide and zinc carbonate; and zinc oxide. The proportion of the amounts of zinc salt [II] to be incorporated is not particularly limited based on the amounts of the compound represented by formula (1), namely, nicotinamides, 3,4-dihydroxy benzoic acid, amino acids, peptides or hinokitiols, and any proportion is employable. Generally, proportions of at least 0.5 fold mols, and routinely 0.5 to 2 fold mols are utilized.

No particular limitation is imposed on the inert solvent, and ordinary inert solvents can be used, inclusive of lower alcohols such as water, methanol, ethanol and propanol; ethers such as dioxane and tetrahydrofuran; dimethylformamides, dimethylsulfoxides and their mixtures.

The reaction can be carried out in the presence of a general deoxidizing agent. Illustrative deoxidizing agents include inorganic carbonates or the like such as ammonia water, sodium hydroxide, sodium carbonate, sodium hydrogencarbonate, sodium hydride and potassium carbonate.

The reaction of the invention proceeds under various conditions without any particular limitations. For instance, the reaction advantageously proceeds at temperatures from room temperature to 100° C. and over 5 minutes to 8 hours.

Among the above-mentioned zinc compounds, zinc dipicolinate can be prepared, for example, by a method described in U.S. Pat. No. 4,315,927. The zinc salts or zinc complexes of amino acids can be prepared, for example, according to the PCT publication of WO86/00004. In case where the zinc salts or zinc complexes which are the effective components of the present invention are incorporated into cosmetic compositions, for example, when solution, gel or colloidal cosmetic compositions are prepared by the use of a solvent such as water, compounds represented by formula (1), namely, pyridinecarboxylic acids, nicotinamide, 3,4-dihydroxy benzoic acid, amino acids, peptides or hinokitiols are added to the solvent, then the above-mentioned ordinary zinc salt [II] is added to the mixture and allowed to react under the mentioned conditions while mixing and stirring, thereby obtaining zinc salts or zinc complexes, which are the effective components of the present invention. They can be used without being isolated or purified. Subsequently, other components of cosmetic bases may be added thereto for preparing desired cosmetic compositions.

It is known that zinc dipicolinate is useful as a therapeutic agent for treating anemia, skin diseases and acrodermatitis enteropathica, and as an agent for ameliorating growth deficiency. It is also reported that zinc dipicolinate shows an excellent anti-arteriosclerosis action ["Arteriosclerosis, Keiji SUZUKI, 18, (11) 983, (1990)]. However, there have been no reports on the use for treating skin diseases caused by exogenous irritative stimulants such as sunburn, psychogenic neurodermatitis, dermatoangiopathy, dermatological symptoms such as psoriasis, erythema multiforme, Behset disease, vericell dermatosis, cement dermatitis, eczema and anogenital pruritus, and radiation sickness such as decreased leukocytes number, loss of hair, flushing of skin, nausea, anorexia and general weariness, let alone reports on the use as a component of cosmetic compositions.

As for the compounds between histidine and zinc, U.S. Pat. No. 4,946,688 discloses their use for treating prostatism, DE-3230292 discloses their use as an food additive, and PCT publication WO87/04622 discloses their use as an amino acid chelating composition which is to be transferred to the tissues of the thyroid gland. The zinc compounds of nicotinamide can also be prepared by known methods.

The aforementioned zinc compounds have an excellent MT inducing function and an action of suppressing SBC caused by UV rays as described in the examples hereinbelow. The zinc salts and zinc complexes are very safe as noted in the case of zinc dipicolinate, for instance, which does not cause any abnormalities by oral administration to adults in amounts of 144 mg/day for 4 weeks ["Agents and Actions", 21, ½, 223–228 (1987)].

When the zinc compounds of the present invention are used as an active component of medicines for treating skin diseases, MT inducing agents, or agents for suppressing SBC, the compounds can be used as they are or together with conventional carriers. No particular limitation is imposed on the manner of administration, and a suitable form is selected as desired. General forms for pharmaceutical agents are available, with illustrative examples including oral agents such as tablets, capsules, granule, and various liquids; non-oral agents such as injections and suppositories; external agents such as liquid applications, lotions, aerosols, liniments, ointments and cataplasms.

The medicines for treating skin diseases, MT inducers and SBC production suppressing agents according to the present invention are useful in the treatment of various skin diseases such as human dermatitis, sunburn, neurodermatitis, dermatoangiopathy, psoriasis, erythema multiforme, Behset disease, varicella dermatosis, cement dermatitis, eczema and anogenital pruritus; radiation sickness such as decreased leukocyte number, loss of hair, flushing of skin, nausea and anorexia, and also in the treatment of skin diseases of non-human mammals (pets including dogs and cats, and domestic animals such as cattle and horses).

The medicines for treating skin diseases, MT inducers and SBC production suppressing agents according to the present invention are prepared according to methods known per se using various diluents, vehicles and the like which are generally employed in medicines.

For instance, among oral-route preparations, tablets are prepared by blending the mentioned zinc compounds together with pharmaceutical vehicles such as gelatin, starch, powdered milk, magnesium stearate, talc, and arabic gum, then given the form of tablets. Capsules are prepared by blending the mentioned zinc compounds with inert pharmaceutical fillers or diluents, and filled in hard gelatin capsules, soft gelatin capsules or the like. Syrups and elixirs are prepared by blending the mentioned zinc compounds together with sweetening agents, such as sucrose, preservatives such as methylparabens and propylparabens, colorants and flavoring agents.

These oral route preparations can also contain carbohydrates, as an energy source, such as vitamins and sucrose; proteins such as casein; amino acids such as methionine; and electrolytes such as NaCl for formulating ameliorants for skin diseases in the dietary therapy; dietary MT inducers; and dietary SBC production suppressing agents.

Non-oral route preparations are prepared, for example, by dissolving the mentioned zinc compounds in sterilized liquid carriers. Preferable carriers are water and saline solution. In the manufacture, liquid agents having a desired transparency and stability, and adaptability to non-oral administration are prepared by dissolving the mentioned zinc compounds in water or an organic solvent, and then in polyethylene glycol having a molecular weight of 200 to 5000. It is preferred that such liquid agents further contain lubricants such as sodium carboxymethylcellulose, methylcellulose, polyvinylpyrrolidone and polyvinylalcohol.

The above-described oral route or non-oral route preparations can further contain sterilizers or mildewproofing agents such as benzyl alcohol, phenol and thimerosal; and furthermore optionally, sucrose, local anesthetics, stabilizers, buffering agents and old ingredients which are known as an UV absorber.

In order to secure the stability, non-oral route preparations may be so prepared that the compositions are charged in capsules or the like, frozen, followed by freeze-drying for removing water. In this case, a liquid can be reproduced from the freeze-dried powder immediately before the use.

No particular limitations are imposed on amounts of the mentioned zinc compounds to be incorporated in oral route or non-oral route preparations. However, it is preferred that the zinc compounds be incorporated into the preparation in amounts from 0.1 to 200 mg per unit dosage. The amounts of the zinc compounds to be administered as an effective component are not particularly limited, and can be suitably selected from a wide range. In order to produce the desired effects, it is preferred that the compounds be administered, in case of adults (body weight: 50 kg), in amounts from 0.1 to 200 mg/day, as divided into 1 to several times a day.

In the manufacture of the medicines for treating skin diseases, MT inducers or agents for suppressing SBC production according to the present invention, known methods can be followed by the use of generally used lipophilic or hydrophilic bases such as fat, fatty oil, lanolin, petrolatum, paraffin, wax, glycols, water and the like.

The above external preparations can optionally contain various additives which are generally known to be added thereto, which include stabilizers, perfumes, colours, etc., and other ingredients known as a UV absorber.

No particular limitations are imposed on the amount of the mentioned zinc compounds to be incorporated in the thus obtained external preparations, and it is suitably determined and selected from a wide range of quantity. However, it is preferred that the zinc compounds be incorporated into the preparation in amounts from about 0.0001 to 30% by weight. Further, a suitable dosage and manner of administration of the present medicines can be varied according to the physical form, amount of active component in the preparation, conditions of the patient such as age, sex and so on, degree of the dermatological disorders, etc. For instance, the medicines of the present invention can be applied to the affected part in such amounts that would sufficiently and completely cover the affected part, from 1 to several times a day by spraying, spreading, or the like.

When the mentioned zinc compounds of the present invention are used as an ingredient of cosmetics for screening UV rays, the cosmetic compositions are prepared into various physical forms by a similar manner employed for preparing general cosmetic compositions, except that the mentioned zinc compounds are incorporated as an active ingredient.

For instance, the cosmetic compositions according to the present invention can be formulated into various forms, for example, skin cleansers; skin care products such as skin lotion, creams, milk lotions, makeup creams, oils and packs; make-up products such as foundations, lipsticks, cheek rouges, eyeliners, mascaras, eyeshadows, manicure preparations and face powders; hair-care products such as hairdressing preparations and hair tonics; bath preparations; whitening preparations; sunscreen preparations; and preparations for treating acne. They are prepared by methods known per se.

In the manufacture of the present cosmetic compositions, various known cosmetic base materials may optionally be added as desired, which include vehicles, binders, lubricants disintegrating agents, etc. Furthermore, other ingredients may be incorporated if needed as long as they do not impede the effects of the invention. Examples of such ingredients include various oleaginous materials, such as oils and fats, waxes, hydrocarbons, fatty acids, higher alcohols, ester oils, metal soaps, etc.; special ingredients such as animal or plant extracts, vitamins, hormones and amino acids, etc.; surfactants; colorants; dyes; pigments; perfumes; preservatives; bactericides; moisturizers; humectants; thickeners; antioxidants; metal sequestering agents; known UV absorbers and other already known various components or additives can be used as necessary in a suitable combination.

In the present cosmetic compositions, the amount of these zinc compounds depends on the physical form, effects of each cosmetic composition and the like. The zinc compounds can be at 0.0001 to 99.9% by weight, preferably about 0.001 to 30% by weight, and more preferably about 0.001 to 10% by weight based on the total weight of the composition. These cosmetic compositions can be used after the dilution with water or some solvents.

EXAMPLES

The details of the present invention are as follows:

EXAMPLE 1

(Effect of zinc dipicolinate on the induction of metallothionein using SHR-SP):

Spontaneously hypertensive rats (SHRs) are derived from Wister-strain Kyoto rats (WKY). The SHRs develop hypertention on the genetic background and most of them die of stroke or myocardial infarction caused by the arteriosclerotic lesions of the blood vessel [Okamoto, K. & Aoki, K., "Jpn. Circ. J., 27, 282–293 (1993)]. A SHR-stroke-prone (SHR-SP) is derived from the SHRs and is attacked by a stroke at a high frequency.

The MT induction by zinc dipicolinate was investigated using SHR-SPs. The SHR-SPs were obtained from Funabashi Nojo (Funabashi, Japan). At the age of 4 to 5 weeks, the rats were divided into three groups. Three rats fed with a feed (manufactured by Funabashi Nojo) and 1% saline solution was used as a control group; nine rats fed with a feed containing zinc dipicolinate (1.5 mg/20 g feed) and 1% saline solution was used as a low concentration group; and 7 rats fed with a feed containing zinc dipicolinate (15 mg/20 g feed) and 1% saline solution was used as a high concentration group.

We observed the amounts of the feed and water ingested by rats. During the observation periods these amounts were not different among the three groups. There was also no difference of body weight in these three groups.

Subsequently, MT induction of the skin of the rat was examined by immunohistochemical staining using anti-rat liver MT antibody. The immunohistochemical staining was carried out by the method previously described (Japanese Patent Application Laid-Open (Kokai) No. 2-247200).

Briefly, the skin specimen were fixed with formation and embedded in paraffin. After cutting by the routine method these skin sections were dehydrated with xylene-alcohol. The skin sections were immersed in a TBS [20 mM Tris, 500 mM NaCl (pH 7.5)] for 10 minutes, immersed in a blocking solution (TBS with 3% gelatin) and then shaked for 5 minutes. After repeating this step, the skin sections were shaked overnight with anti-rat MT rabbit IgG (1:400; diluted with TBS +1% gelatin).

Subsequently, the skin sections were washed with TTBS solution (TBS with 0.05% Tween-20) and shaked for 5 minutes. After repeating this step, the sections were immersed with horse radish peroxidase-conjugated goat anti rabbit IgG antibody (1:400) and shaked for more than 1 hour. Further, the skin sections were washed with TTBS and shaked for 5 minutes. After repeated twice, this step was conducted once again. After washing with TTBS, the skin sections were immersed in a development solution (20% cold methanol, 0.06% DAB, and 0.018% $H_2O_2$ in TBS) and shaked for 45 minutes. The sections were rinsed briefly with distilled water, air-dried, photographed and immunoassayed.

Table 1 shows the immunohistochemical findings of the epidermis, sebaceous glands, and hair follicles of the rat skin using MT antibody.

In the table, (−) indicates negative, (+) indicates weakly positive, (++) indicates positive, (+++) indicates strongly positive.

From these results, zinc dipicolinate is considered to promote the induction of MT, and zinc dipicolinate is highly expected to the useful agent in the treatment of various skin diseases. In addition, since a strong effect was observed by oral administration, zinc dipicolinate is also expected to be effective for topical application.

EXAMPLE 2

(Effect of zinc dipicolinate on the UV-induced skin damage):

As a light source of UV irradiation, DERMARAY-100 (Clinical Supply) equipped with FL20SE-30 fluorescent sunlight lamp tubes (Toshiba) was used. The degree of UV-induced skin damage was evaluated by the number of SBCs in the epidermis and the swelling of the earlobe after UV irradiation.

Five BALB/c mice (age: 5 weeks) were used. A 10% ethyl alcohol solution containing 1.0% zinc dipicolinate was applied three times to the outer surface of right earlobe of each mouse. As a control, 10% ethyl alcohol solution was applied three times to the left side of the earlobe of each mouse. Twenty-four hours after the third application, both of earlobes were irradiated with UV light at a dose of 100 $mJ/cm^2$. Twenty-four hours after the irradiation, the irradiated skin was biopsied and processed to the routine histological examinations.

Each samples was stained with hematoxylin and eosin, and then counted the number of SBCs in the epidermis of the ear skin.

The swellings of the earlobe was measured by a thickness gage (Okazaki Mfg. Co.,) and the degree of swelling was evaluated by the increase of the thickness of the earlobe after UV irradiation.

Figure 2:
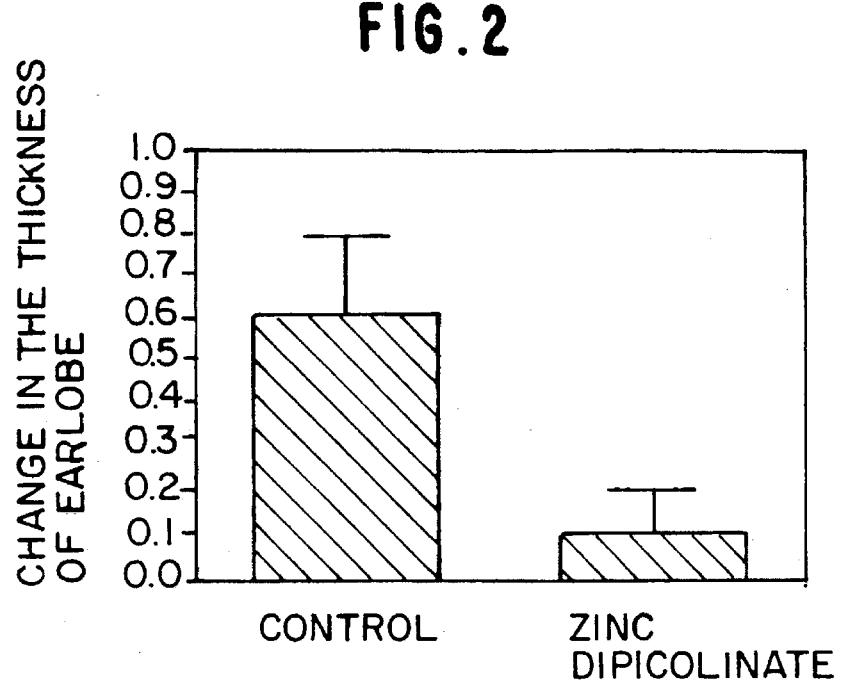
FIG. 2 is a graph which shows the change in the thickness of the external ear before and after UV radiation.

The results are shown in FIGS. 1 and 2.

FIG. 1 shows the number of SBCs formed in the epidermis (per 1 cm) after UV irradiation. In the control group, the number of SBCs was 19.6±3.2 (M±S.E.), whereas in the group applied topically with zinc dipicolinate, the number of SBCs was 15.4±2.1 (M±S.E.). This result indicates that zinc dipicolinate reduced the cell damage induced by UV irradiation.

FIG. 2 shows the thickness of the earlobe (degree of swelling) before and after UV irradiation. In the control group, the thickness was 0.6±0.12 mm (M±S.E.), whereas in

TABLE 1

| Control group | | | Low concentration group | | | High concentration group | | |
|---|---|---|---|---|---|---|---|---|
| Epidermis | Sebaceous glands | Hair follicles | Epidermis | Sebaceous glands | Hair follicles | Epidermis | Sebaceous glands | Hair follicles |
| − | − | − | − | − | − | − | + | + |
| ++ | − | + | ++ | ++ | ++ | + | + | − |
| − | − | − | − | ++ | − | + | ++ | − |
| | | | − | + | − | ++ | + | + |
| | | | − | + | − | +++ | + | + |
| | | | + | + | − | − | + | − |
| | | | − | + | − | + | + | + |
| | | | ++ | + | − | | | |
| | | | + | + | − | | | |

The data of Table 1 demonstrated that the MT was scarcely induced in the control group. In the groups fed with zinc dipicolinate, on the contrary, MT was strongly induced in the epidermis, sebaceous glands or hair follicles. The intensity of the MT induction correlated with the concentration of zinc dipicolinate used in this experiment.

group applied with zinc dipicolinate, the thickness was 0.1±0.10 mm (M±S.E.), which indicates the swelling of the earlobe was significantly suppressed by zinc dipicolinate.

From these results, it is suggested that zinc dipicolinate is a useful agent in the treatment of the skin diseases such as UV-induced dermatitis. Zinc dipicolinate is also useful as a cosmetic component for ameliorating and preventing the sunburn.

EXAMPLE 3

(Effect of zinc dipicolinate on the induction of metallothionein):

In order to investigate the induction of metallothionein mRNA by zinc dipicolinate, a northern blot hybridization was carried out using human metallothionein-IIA cDNA as a probe.

Human metallothionein-IIA cDNA (hMT-IIA cDNA: ATCC57153, U.S.A.) was used as probe. This hMT-IIA cDNA is 400 bases DNA fragment designed from the restriction endonuclease EcoRI-HindIII region of the human metallothionein gene ["Cell", 37, 263–272 (1984): "Nature", 299, 797–802 (1982): "Nucleic Acids Res.", 15, 10949 (1987)]. To obtain a probe this fragment was labeled with a-[$^{32}$P]-dCTP using a multi-prime DNA labeling system (Amersham Co.) based on the multi-prime DNA labeling method ["Anal. Biochem", Feinberg, A. P., et al., 137, 266–267 (1984). By the same method, beta-actin cDNA was labeled with $^{32}$p.

HT-1376 cells are an epidermal cell strain which was established from human bladder cancer, and this characterization of this cell line was reported in Nat Cancer Inst., 58, 881–890 (1977). This cells are deposited at the ATCC (American Type Culture Collection) with a deposit number of ATCC CRL 1472.

The HT-1376 cells were cultured 5% fetal bovine serum (FBS) but free from corticosteroid or epidermal growth factor (EGF) at 37° C. in 5% $CO_2$ for 4 days.

The HT-1376 cells ($6 \times 10^5$/dish) were inoculated in 16 culture dishes which are 10 cm in diameter. To 4 dishes, zinc dipicolinate was added, final concentration was arranged to 5 µM in the culture medium. As a positive control, cadmium chloride (Sigma Co.) was administered to 4 dishes with final concentration of 10 µM. The culture dishes containing only medium was used as negative controls.

The culture dishes containing the substances as mentioned above were cultured at 37° C. for 24 hours, followed by exposing the substances. The cells were washed with phosphate-buffered saline (PBS), and were collected by centrifugation (1000 rpm×5 min.). From these cells, the whole RNA was extracted by the method of density-gradient centrifugation using guanidine thiocyanate.cesium trifluoro acetic acid ("Molecular Cloning", Sambrook, et al., 7–9, Cold Spring Harbor Laboratory, 1989).

One gram of 1.2% agarose was added to a mixture of 10 ml of 10× MOPS buffer solution [0.2M morphorinopropane sulfonic acid(MOPS), pH 7.0, 50 mM sodium acetate, 10 mM EDTA] and 85 ml of a double-distilled water, and dissolved by autoclave for 5 minutes. To prepare a gel, after cooling the mixture to approximately 60° C., 5.5 ml of 37% deionized formaldehyde was added, stirred, and transfer to the tray. An appropriate amount of RNA was precipitated with ethanol and dried. Twenty micrograms of the whole RNA was dissolved in a sample buffer solution [1× MOPS buffer, 2.2M formaldehyde, 50% formamide, 10 mM EDTA], and heated at 65° C. for 15 minutes, and added with 2 µl of solution containing 0.5 mg/ml of ethidium bromide [50% glycerol, 0.1% bromophenol blue, 0.1% xylene cyanole]. Subsequently, electrophoresis was carried out using a buffer solution containing 100 ml of 10× MOPS buffer, 55 ml of formaldehyde and 850 ml of water at 100 V for 2 to 3 hours.

After photographs were taken, the gel immersed twice in 10×SSC [1× SSC, 0.15M NaCl, 0.015M sodium citrate] for 20 minutes each, and shaked slowly for removing formaldehyde. Then, the whole RNA was blotted to the nitrocellulose filter for 12 hours using 20× SSC.

After blotting the filter was air-dried at room temperature, and baked at 80° C. for 2 hours.

After the filter was moistened with 3× SSC, prehybridization was carried out using a prehybridization solution [5× SSC, 50% formaldehyde, 50 mM sodium phosphate, 100 µg/m]. heat-denatured salmon sperm DNA, 1% SDS, 10× Denhart solution (1× Denhart solution, 0.02% bovine serum albumin, 0.02% ficoll, 0.02% polyvinylpyrrolidone)] at 43° C. for 2 to 3 hours.

Then, a hybridization solution [prehybridization liquid, 10% dextran sulfate, 2 to $3 \times 10^6$ cpm/ml labelled probe (a probe which was denatured in boiling water and quenched)] was used instead of the above-mentioned prehybridization solution, and hybridized at 43° C. for 20 hours.

After the hybridization, the filter was washed with 2×SSC, and the re-hybridization was carried out at 43° C. for 20 hours using beta-actin cDNA as a labeled probe.

The filter was washed twice with 2× SSC and then washed twice with 0.2× SSC containing 0.1% SDS at 65° C. for 30 minutes. After drying at room temperature, the filter was fixed to a filter paper, and placed in the X-ray film cassette. Then the X-ray film (Kodak) was superposed on the filter and was exposed at −70° C. for 48 hours.

As a result, similar to the effect of cadmium, zinc dipicolinate also enhanced the expression of metallothionein mRNA. Due to the high toxicity, cadmium cannot be used to human. In contrast to cadmium, zinc dipicolinate is highly safe as described above. From these results, zinc dipicolinate is considered to be useful as an MT protein inducer in human.

EXAMPLE 4

(Effects bis (2,5-pyridine dicarbosylate) zinc.2Na (abbreviated as "bis zinc.2Na salts") on the UV-induced skin damage):

As a light source of UV irradiation, an irradiation apparatus equipped with 2 light tubes of FL20SE health care fluorescent lamp (Toshiba) was used.

The degree of UV-induced damage was examined by the number of SBC in the epidermis after UV irradiation.

Eight hairless mice [BALB/cA Jcl-hr, Nihon Crea Co. (age: 8 weeks)] were used. An aqueous solution of 1% bis zinc.2Na salt was topically applied to the skin of the trunk of 6 mice 3 times every 8 hours. As a control another two mice were applied with distilled water at their skin of the trunk 3 times every 8 hours. Twenty-four hours after the irradiation, the mice were sacrificed, and the skin was biopsied. The tissues were fixed with 10% formalin to prepare the tissue slice samples.

Each skin section was stained with hematoxylin and eosin, and then the number of SBCs was counted in the length of 1 mm. The results are shown in Table 2.

TABLE 2

| Treatment with | Number of SBCs ( /mm) | Mean ± SE |
|---|---|---|
| Distilled water | 3, 5 | 4.0 ± 1.4 |
| 1% Bis zinc.2Na salt | 4, 0, 1, 2, 1, 0 | 1.3 ± 1.5 |

The data of table 2 shows that in the control group the number of SBCs is 4.0±1.4, whereas in the treated group, the number is 1.3±1.5 (M±S.E.). These data indicate that the bis zinc.2Na salt reduces the UV-induced skin damage.

From these results, it is suggested that bis zinc.2Na salt is a useful agent in the treatment of skin diseases such as UV-induced dermatitis. Bis zinc.2Na salt is also useful as a cosmetic component for ameliorating and preventing the sunburn.

EXAMPLE 5

(Effect of bis(L-histidinolate) zinc(II) (His-Zn) on the induction of MT using rats:

Five male Wistar rats[age: 7 seeks, body weight: 180–200 g, specific pathogen-free rat (Nihon Crea Co. ) were fed with a feed (CE-2, Nihon Crea Co. ) for 1 week. After the inspection normal rats only were subjected to the experiment. The compound (His-Zn) used in the Example 3 was suspended in 10 ml of water and dissolved by sonication. This compound was administered to each rat via oral route using stomach probe at a dose of 100 mg/10 ml/kg per day. As a control, 5 rats were fed without this compound. After 12 and 24 hours of the administration of the compound, the MT concentration in the liver was determined. The quantitative analysis of the MT was performed by the radioimmunoassay reported by Nakajima et al. ["Methods in Enzymology" Nakajima, K., et al., 205, 388–395 (1991)].

This is, the excised rat liver was homogenized with 50 mM Tris-HCl (pH 8.5, diluted to 1:5-10), and centrifuged (4000×g) at 4° C. for 30 minutes. The supernatant was submitted to a heat treatment in boiling water for 3 minutes, followed by cooling down to 4° C.

Subsequently, this extract was centrifuged (2000×g) at 4° C. for 20 minutes. To prepare the test sample, the supernatant was diluted with standard diluent solution (50 mM phosphate buffer solution containing 0.25% bovine serum albumin (BSA), 10 mM EDTA.2Na, and 0.01% NaN$_3$ (pH 7.4)]. The radioimmunoassay for MT was performed as follows:

First, 200 µl of the standard diluent solution, 100 µl of anti-MT rabbit serum (diluted in 1:20,000), 100 µl of the test sample and 100 µl of $^{125}$I-labeled-thyrosine-MT (about 10,000 cpm) were added to the 10×75 mm glass tube. This mixture was incubated at 4° C. for 48 hours. Then, goat anti-rabbit IgG serum and the normal rabbit serum, which were diluted completely with standard diluent solution, were added. Finally, 200 µl of 12.5% polyethylene glycol was added. After incubating at room temperature for 30 minutes, the reaction mixture was centrifuged (3,000 rpm) at 4° C. for 30 minutes. The radioactivities of the supernatant and precipitates were examined with a gamma counter.

The results are sown in Table 3.

TABLE 3

|  | Metallothionein (µg/g liver) | |
| --- | --- | --- |
|  | 12 hours | 24 hours |
| Control group | 4.4 ± 2.0 | |
| Test group | 117.0 ± 56.1 | 32.4 ± 9.0 |

From the data of Table 3, in the control group MT concentration of the liver was 4.4±2.0 µg/g liver. In the test group after 12 and 24 hours of administration, MT concentration of the livers were 117.0±56.1 and 32.4±9.0 µg/g liver, respectively. These data indicate that MT is highly induced by the administration of His-Zn.

From these results, it is suggested that the His-Zn has the MT inducing effect. So, His-Zn is highly expected as a useful agent for the treatment of various skin diseases, reducing the SBCs formation, and the protection of radiation-induced or UV-induced damage.

Since His-Zn is a potent inducer of MT by oral administration, it is expected that His-Zn is also effective by topical application.

Preparation Example 1:

Dihinokitiolato zinc(II):

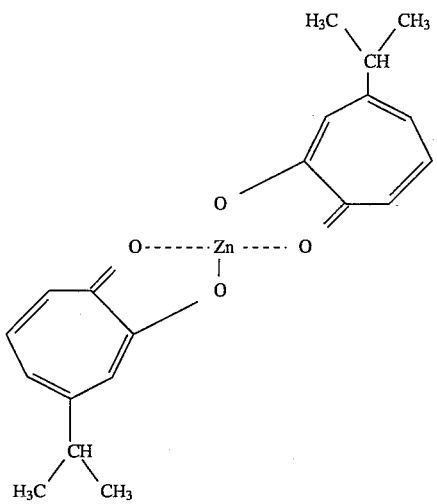

Hinokitiol used was supplied by Takasago Koryo Kogyo K.K., zinc acetate.2H$_2$O, and ethanol were guaranteed grade of Wako Pure Chem. Industries Ltd., all of which were used without further purification. 5.0 g of hinokitiol was dissolved in ethanol with stirring, to which 3.4 g of zinc acetate.2H$_2$O was added and dissolved. The mixture was stirred for 5 hours, and the precipitates were filtrated with a No. 5C filter paper followed by drying under reduced pressure using a vacuum pump (Vacuum Pump 4VP-C$_4$; manufactured by K.K. Hitachi Ltd.) to obtain 4.6 g of dihinokitiolate zinc(II) or dihinokitiolato zinc(II).

Preparation Example 2:

Zinc nicotinate (Compound A):

The reagents used were of guaranteed grade nicotinic acid (Kanto Chem Co., Inc.), Zinc acetate.2H$_2$O and ammonia water (Wako Pure Chem. Industries Ltd.)

5.0 g of nicotinic acid was dissolved in 100 ml of deionized water with stirring in a hot bath. Similarly, 4.5 g of zinc acetate.2H$_2$O was dissolved in 100 ml of deionized water in a hot bath, and both were mixed with vigorous stirring. Subsequently, ammonia water (1:1 mixture of 25% ammonia water and distilled water) was added to adjust the pH to 8.5. The mixture was heated in a hot bath of about 80° C. for 10 minutes to complete the reaction, was continuously applied to concentrate the mixture, then being evaporated to about 20 ml. After cooling in a refrigerator, the precipitate was filtrated with a No. 5B filter paper, and washed with deionized water. The obtained material was dissolved with heating in 200 ml of deionized water, followed by concentration to 20 ml. The concentrate was cooled at room temperature, and washed three times with deionized water. The obtained material was dried sufficiently at 65° C. in an electric oven to obtain 3.0 g of zinc nicotinate (hereinafter abbreviated as Compound A).

Crystal form: White powder or white plates

Elemental analysis:
Experimental (%): C 45.60
 H 2.83
 N 8.92
 Zn 21.16

The above experimental values agreed with the following calculated ratio:

Nicotinic acid:Zinc:H$_2$O=2:1:0

NMR spectrum: NMR spectrum was measured using an apparatus, JNM-GSX270 (manufactured by Nihon Denshi):
 Solid $^{13}$C-NMR δ ppm; 172.5 (C=O) 150.1 (C-6,2) 139.7 (C-4) 132.5 (C-3) 125.5 (C-5)

| IR spectrum: | |
|---|---|
| Nicotinic acid (starting material): | |
| 2200–3000 cm$^{-1}$ | m (COOH stretching vibration) |
| 1730 | s (C=O stretching vibration of carboxylic acid) |
| 1419 | m (C—O—H deformation vibration) |
| 1330, 1305 | s (C—O stretching vibration) |
| Zinc nicotinate (Compound A): | |
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration) |

From the above data, nicotinic acid is suggested to have a free carboxyl group, that is, it is not a dimer, whereas Compound A is considered to be a carboxylate.

Figure 3:
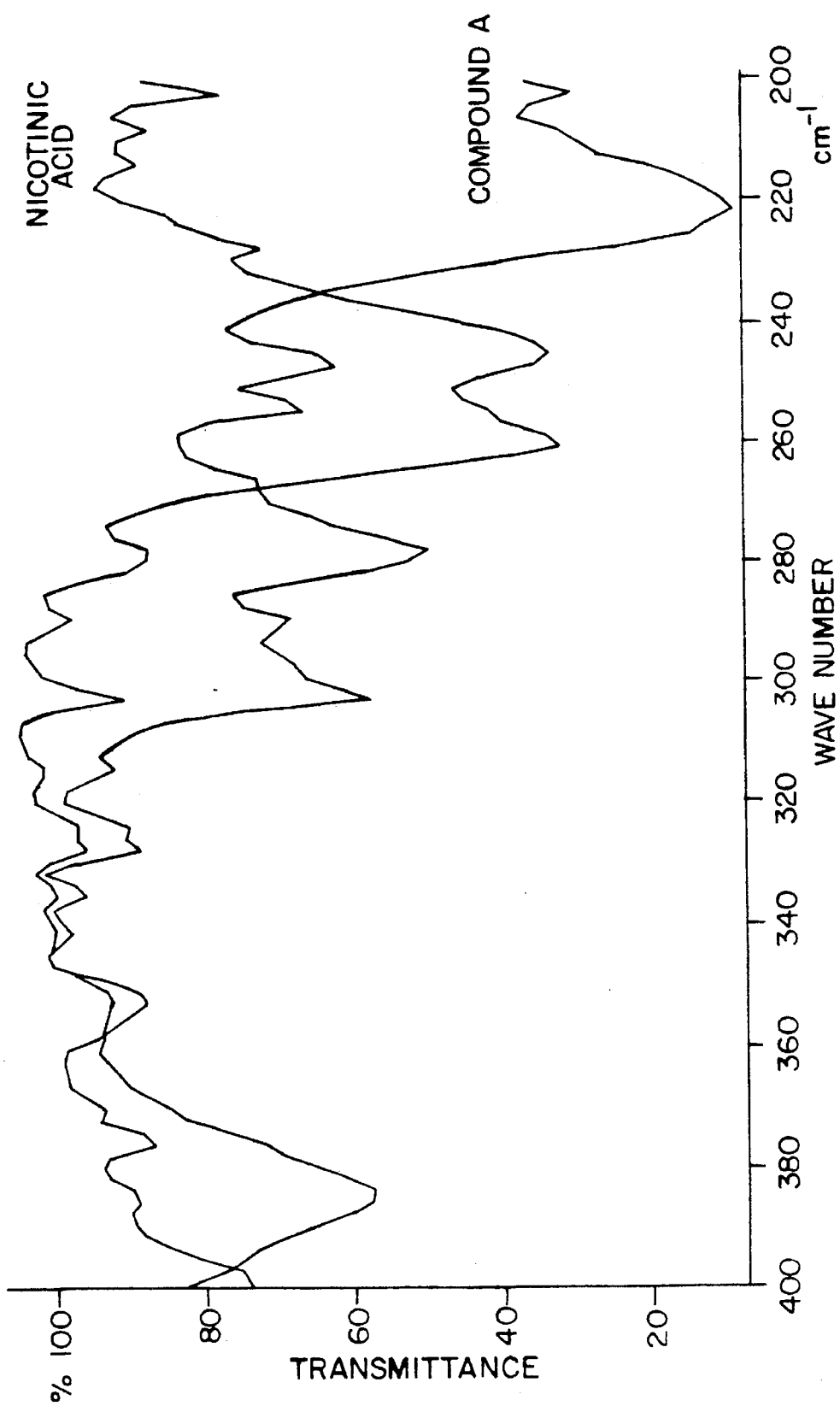
FIG. 3 is an IR spectrum of compound A obtained in the Preparation Example 2 and its starting material, nicotinic acid, at the wave number of 200–400 cm$^{-1}$.

Moreover, from the IR spectrum of-wave number 200 to 400 cm$^{-1}$, it was considered that the peak in the vicinity of 200 cm$^{-1}$ in FIG. 3 was attributed to the bond of zinc and nitrogen, and therefore, nicotinic acid and zinc were bonded by way of the ionic bonding or coordinate bonding.

Preparation Example 3:

Bis(L-histidinolato)zinc(II):

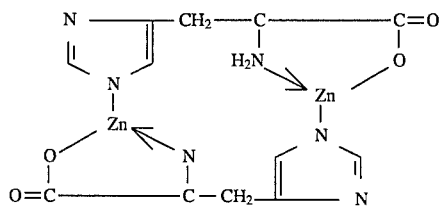

L-Histidine, zinc sulfate.7H$_2$O and sodium hydrogencarbonate were guaranteed grade of Wako Pure Chem Industries Ltd., all of which were used without further purification.

7.4 g of zinc sulfate.7H$_2$O was dissolved in 60 ml of deionized water with stirring in a water bath. To this solution was added 6.4 g of sodium hydrogencarbonate with vigorous stirring. The reaction was allowed to complete by heating the mixture at 80° C. for 10 minutes to produce zinc carbonate. With further vigorous stirring, 8.0 g of L-histidine was added to this solution, and the reaction was allowed to complete by heating the mixture at 80° C. for 10 minutes. The mixture was there evaporated to about 30 ml, and then cooled down at room temperature. The precipitated complexes were filtrated with a No. 5C filter paper, followed by washing and decanting with 50 ml of water. The supernatant was removed with a capillary. The crystals was washed 200 ml of deionized water in a water bath, decanted and the supernatant removed was repeated three times for purification. The obtained material was dried sufficiently at 65° C. in an electric oven to obtain 5.6 g of zinc(II) bis(L-histidinolato).

Preparation Example 4:

Zinc(II) bis(3,4-dihydroxybenzoato):

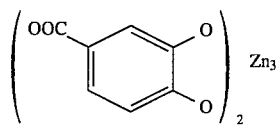

3,4-Dihydroxybenzoic acid (protocatechuic acid) was provided by Tokyo Kasei Kogyo Co., Ltd., and zinc acetate.2H$_2$O, methanol and sodium hydroxide were of guaranteed grade of Wako Pure Chem. Industries Ltd., all of which were used without further purification.

7.0 g of zinc acetate.2H$_2$O was dissolved in 40 ml of deionized water with stirring in a water bath. Similarly, 5.0 g of protocatechuic acid was dissolved in 10 ml of methanol in a water bath, to which 20 ml of deionized water was added. Both were vigorously stirred and mixed. Subsequently, a NaOH solution (diluted to 0.25 mol/1) was added adjusting the pH to 5.5 (by the use of a pH meter). The reaction was allowed to complete by heating the mixture in a water bath at about 80° C. for 10 minutes. The mixture was there evaporated about 20 ml, then cooled down with ice. The precipitated complexes were filtrated with a No. 5C filter paper, followed by washing with deionized water. A procedure of washing and filtrating with 200 ml of deionized water and methanol was repeated three times to purify the product. The obtained product was dried sufficiently at 65° C. or lower temperatures in an electric oven to obtain 4.0 g of bis(3,4-dihydroxybenzoato)zinc(II).

Preparation Example 5:

Bis(2,5-pyridine carboxylato)zinc(II).2Na:

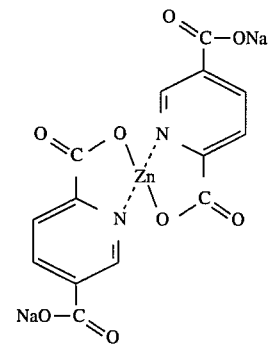

2,5-Pyridine dicarboxylic acid, anhydrous sodium carbonate, and Zinc(II) acetate.2H$_2$O, were of guaranteed grade of Wako Pure Chem. Industries Ltd., all of which were used without further purification.

1.0 g of 2,5-pyridine dicarboxylic acid and excess sodium carbonate in 15 ml of distilled water were mixed under stirring.

After completing CO$_2$ generation, a small amount of sodium carbonate, then excess zinc acetate.2H$_2$O, were added to the mixture, and stirred for 15 to 30 min. The precipitate was filtered with a No. 5B filter paper, followed by drying under reduced pressure using a vacuum pump (Vacuum Pump 4VP-C$_4$; manufactured by Hitachi Ltd.) to obtain 0.7 g of bis(2,5-pyridine dicarboxylato)zinc(II).2Na.

Crystal Form: White powder

Solvent used for the NMR measurement: A solution was prepared with $D_2O$ (heavy water) so that the concentration is suitable for the NMR measurement (1% or less), and NMR spectrum was measured using an apparatus, Gemini-200M (manufactured by Varian Co.).

$^1$H-NMR($D_2O$ $\delta$: 8.25 (2H, d, J=7.88 Hz), 8.47 (2H, d), 8.83 (2H,s)

Preparation Example 6:

Nicotinamide zinc (Compound B):

4.89 g (0.04 mol) of nicotinamide is dissolved in 100 ml of ethanol, to which 2.73 g (0.02 mol) of $ZnCl_2$ in a 50 ml ethanol is added and mixed. When stirred, white crystals immediately precipitate. The precipitate is filtrated with a No. 5C filter paper, followed by washing with ethanol and then diethylether. The washed product is allowed to stand for evaporating diethylether, and dried at 60° C. in an electric oven to obtain the target compound.

Elemental analysis: Calculated (%): C: 37.87 H: 3.18 N: 14.72 Zn: 17.18

Experimental (%): C: 37.41 H: 3.18 N: 14.42 Zn: 18.62

The above experimental values agreed with the following calculated ratio:

Nicotinamide:Zinc =2:1

IR spectrum:

Nicotinamide (starting material):

| | | |
|---|---|---|
| 3200–3500 cm$^{-1}$ | s | (NH stretching vibration based on —CO—NH$_2$$^-$) |
| 1683 | s | (C=O stretching vibration |
| 1623 | m | (—N—H deformation vibration) |

Nicotiamide zinc (Compound B):

| | | |
|---|---|---|
| 3200–3500 cm$^{-1}$ | s | (NH stretching vibration based on —CO—NH$_2$—) |
| 1683 | s | (C=O stretching vibration) |
| 1608 | m | (—N—H deformation vibration) |

From the above data, nicotiamide zinc has a broader NH stretching vibration based on —CO—NH$_2$ at 3200–3500 cm$^{-1}$ than nicotinamide, and further, since the N—H deformation vibration of the pyridine ring at the vicinity of 1650 cm$^{-1}$ is somewhat varied, it was presumed that nicotinamide and zinc were bonded via a coordinate bonding.

UV spectrum: The product was dissolved in ethanol and the UV spectrum was measured.

| Peak | | Valley | |
|---|---|---|---|
| λ | Absorption | λ | Absorption |
| Nicotinamide (starting material): | | | |
| 262.4 | 0.715 | 245.8 | 0.549 |
| 217.6 | 1.779 | | |
| Zinc nicotinamide | | | |
| 262.6 | 0.498 | 246.4 | 0.380 |
| 216.4 | 1.407 | | |

Preparation Example 7:

Picolinamide zinc (Zn:picolinamide=1:1) (Compound C):

1.83 g (0.015 mol) of picolinamide zinc is dissolved in 35 ml of ethanol, to which 2.04 g (0.015 mol) of $ZnCl_2$ in a 40 ml ethanol solution is added and mixed, followed by stirring overnight to prepare an ethanol solution containing 0.2M of zinc picolinamide.

Preparation Example 8:

Picolinamide zinc (Zn:picolinamide=1:2) (Compound D):

3.66 g (0.03 mol) of zinc picolinamide is dissolved in 75 ml of ethanol, to which 2.04 g (0.015 mol) of $ZnCl_2$ in a 40 ml ethanol solution is added and mixed, followed by stirring overnight to produce a very small amount of white crystals. The crystals are filtrated with a No. 5C filter paper, and washed with ethanol and then with diethylether. The obtained product is allowed to stand for evaporating diethylether and dried in an electric drying apparatus at 60° C. to prepare the target compound.

Elemental analysis: Calculated (%): C: 37.87 H: 3.18 N: 14.72 Zn: 17.18

Experimental (%): C: 37.46 H: 3.15 N: 14.50 Zn: 18.69

The above experimental values agreed with the following calculated ratio: Picolinamide: Zinc=2:1

EXAMPLE 6:

Tablets (Formula)

| | |
|---|---|
| (1) Zinc dipicolinate | 10 g |
| (2) Lactose (Japanese Pharmacopoeia) | 40 |
| (3) Corn starch (Japanese Pharmacopoeia) | 20 |
| (4) Crystalline cellulose (Japanese Pharmacopoeia) | 20 |
| (5) Hydroxypropylcellulose (Japanese Pharmacopoeia) | 5 |
| (6) Magnesium stearate (Japanese Pharmacopoeia) | 2 |

(Method of preparation)

A thorough mixture of ingredients (1)–(4) and (6) above along with a 5% aqueous solution of ingredient (5) was made into granules, passed through a 200-mesh sieve, carefully dried, and tabletted by a method known per se to prepare 1000 tablets.

EXAMPLE 7

Hydrophilic petrolatum ointment:

(Formula)

| | |
|---|---|
| (1) Zinc dipicolinate | 1 g |
| (2) Stearyl alcohol | 220 |
| (3) White petrolatum | 250 |
| (4) Propyl parahydroxybenzoate | 0.15 |
| (5) Methyl parahydroxybenzoate | 0.25 |
| (6) Propylene glycol | 120 |
| (7) Sodium lauryl sulfate | 15 |
| (8) Purified water | a sufficient quantity |
| Total: | 1000 |

(Method of preparation)

(I) According to the process described in the Pharmacopoeia of Japan (9th edition, Part II), under the heading of hydrophilic ointment, ingredients (2)–(3) were melted on a water bath, stirred, and kept temperature of the mixture at 75° C.

(II) Ingredients (1), (4)–(7) above were added to the purified water of ingredient (8) above, followed by warming and dissolving to prepare an aqueous solution of 75° C.

(III) Subsequently, is added the above aqueous solution obtained in step (II) to the above mixture formed in step (I), followed by stirring thoroughly until it congealed to obtain the target hydrophilic ointment.

EXAMPLE 8

Vanishing cream:

| (Formula) | |
|---|---|
| (1) Stearic acid | 10.0 wt. % |
| (2) Paraffin wax (135F) | 2.0 |
| (3) Spermaceti | 2.0 |
| (4) Cetyl alcohol | 2.0 |
| (5) Cetyl isooctanoate | 5.0 |
| (6) Polyoxyethylene sorbitan monolaurate (20EO) | 3.0 |
| (7) Butyl parahydroxybenzoate | 0.1 |
| (8) Methyl parahydroxybenzoate | 0.1 |
| (9) Sodium hydroxide | 0.15 |
| (10) Concentrated glycerin | 5.0 |
| (11) Compound A | 0.5 |
| (12) Perfume | a sufficient quantity |
| (13) Purified water to make total: | 100.0 |

(Method of preparation)

(I) Ingredients (1) to (7) were heated at 80° to 85° C. and uniformly melted.

(II) Ingredients (8) to (11) and the purified water of (13) were heated at 80° to 85° C. and uniformly dissolved.

(III) Subsequently, the solution (II) was added to solution (I) in portions at 80° C., and after a smooth emulsion was formed, the emulsion was cooled to 45° C. with stirring.

(IV) After the perfume of ingredient (12) above was added to (III) at 45° C., the mixture was uniformly stirred, and then cooled to room temperature with stirring.

The vanishing cream thus obtained was a stable emulsion.

EXAMPLE 9

Cleansing cream:

| (Formula) | |
|---|---|
| (1) Bleached beeswax | 3.0 wt. % |
| (2) Liquid petrolatum | 30.0 |
| (3) Cetyl alcohol | 2.0 |
| (4) Cetyl isooctanoate | 10.0 |
| (5) Butyl parahydroxybenzoate | 0.1 |
| (6) Methyl parahydroxybenzoate | 0.1 |
| (7) Triethanolamine | 0.2 |
| (8) Propylene glycol | 5.0 |
| (9) Zinc dipicolinate | 0.1 |
| (10) Antioxidant | a sufficient quantity |
| (11) Perfume | a sufficient quantity |
| (12) Purified water to make total: | 100.0 |

(Method of preparation)

Ingredients (1) to (12) were blended as described in Example 8 and emulsified. A stable emulsion was obtained.

EXAMPLE 10

Milk lotion:

| (Formula) | |
|---|---|
| (1) Stearic acid | 3.0 wt. % |
| (2) Spermaceti | 3.0 |
| (3) Glyceryl monostearate, lipophilic | 2.0 |
| (4) Bleached beeswax | 2.0 |
| (5) Saturated fatty acid (C8–C12) triglyceride | 10.0 |
| (6) Butyl parahydroxybenzoate | 0.1 |
| (7) Methyl parahydroxybenzoate | 0.1 |
| (8) L-arginine | 1.0 |
| (9) Sorbitol | 3.0 |
| (10) Bis(L-histidinolate)zinc(II) or Bis(L-histidinolato)Zinc(II) | 0.3 |
| (11) Perfume | 0.1 |
| (12) Purified water to make total: | 100.0 |

(Method of preparation)

Ingredients (1) to (12) were blended as described in Example 8 and emulsified. A stable emulsion was obtained.

EXAMPLE 11

Make-up cream:

| (Formula) | |
|---|---|
| (1) Cetyl alcohol | 2.0 wt./% |
| (2) Stearic acid | 5.0 |
| (3) Glyceryl monostearate, self-emulsifying | 2.0 |
| (4) Butyl parahydroxybenzoate | 0.1 |
| (5) Titanium oxide | 1.0 |
| (6) Iron oxide pigment | 0.5 |
| (7) Methyl parahydroxybenzoate | 0.1 |
| (8) 2-Amino-2-methyl-1,3-propanediol | 1.0 |
| (9) Polyethylene glycol 1500 | 3.0 |
| (10) Bis(3,4-dihydroxybenzoate)zinc (II) or Bis(3,4-dihydroxybenzoato)zinc (II) | 0.5 |
| (11) Perfume | a sufficient quantity |
| (12) Purified water to make total: | 100.0 |

(Method of preparation)

Ingredients (1) to (12) were blended as described in Example 8 and emulsified. A stable emulsion was obtained.

EXAMPLE 12

Nourishing cream:

| (Formula) | |
|---|---|
| (1) Bleached beeswax | 10.0 wt. % |
| (2) Batyl alcohol | 1.0 |
| (3) Squalane | 20.0 |
| (4) Glyceryl trioctanoate | 20.0 |
| (5) Glyceryl monostearate, lipophilic | 2.0 |
| (6) Polyoxyethylene sorbitan monolaurate (20EO) | 2.0 |
| (7) Propyl parahydroxybenzoate | 0.1 |
| (8) Methyl parahydroxybenzoate | 0.1 |
| (9) Concentrated glycerin | 5.0 |
| (10) Dihinokitiolate zinc (II) or Dihinokitiolato zinc (II) | 0.02 |
| (11) Antioxidant | a sufficient quantity |
| (12) Purified water to make total: | 100.0 |

(Method of preparation)

Ingredients (1) to (12) were blended as described in Example 8 and emulsified. A stable emulsion was obtained.

EXAMPLE 13

W/O cream:

| (Formula) | |
|---|---|
| (1) Bleached beeswax | 10.0 wt. % |
| (2) Batyl alcohol | 3.0 |
| (3) Liquid petrolatum | 30.0 |
| (4) Glyceryl trioctanoate | 20.0 |
| (5) Butyl parahydroxybenzoate | 0.2 |

21
-continued

| (Formula) | |
|---|---|
| (6) Lecithin | 5.0 |
| (7) Zinc dipicolinate | 0.1 |
| (8) Antioxidant | a sufficient quantity |
| (9) Purified water to make total: | 100.0 |

(Method of preparation)

Ingredients (1) to (9) were blended as described in Example 8 and emulsified. A stable emulsion was obtained.

EXAMPLE 14

Pack (peel-off type):

| (Formula) | |
|---|---|
| (1) Polyvinyl alcohol | 15.0 wt. % |
| (2) Polyvinylpyrrolidone | 5.0 |
| (3) Methyl parahydroxybenzoate | 0.2 |
| (4) Concentrated glycerin | 5.0 |
| (5) Dihinokitiolate zinc(II) or Dihinikitiolato zinc(II) | 0.0001 |
| (6) Ethyl alcohol | 15.0 |
| (7) Purified water to make total | 100.0 |

(Method of preparation)

To the purified water of ingredient (7) above, the polyvinyl alcohol of ingredient (1) damped with part of the ethyl alcohol and the polyvinylpyrrolidone of ingredient (2) were added. The mixture was heated to 70° C. while temporarily stirred, and allowed to stand for 1 day. On the following day, ingredients (4) and (5) and the remainder of ingredient (6) were added to the mixture, and uniformly stirred. Thereafter, the mixture was cooled to room temperature with stirring to obtain a pack composition.

EXAMPLE 15

Lotion:

| (Formula) | |
|---|---|
| (1) Ethyl alcohol | 10.0 wt. % |
| (2) Polyoxyethylene laurylether (9EO) | 2.0 |
| (3) Photosensitizing Dye No. 201 | 0.001 |
| (4) Perfume | a sufficient quantity |
| (5) Concentrated glycerin | 5.0 |
| (6) 1,3-butylene glycol | 3.0 |
| (7) Bis(2,5-pyridine carboxylato)zinc II.2Na salt | 0.05 |
| (8) Colour | a sufficient quantity |
| (9) Purified water to make total: | 100.0 |

(Method of preparation)

(I) Ingredients (2) to (4) were added to the ethyl alcohol of ingredient (1) and mixed to a uniform solution.

(II) Ingredients (5) to (7) were added to the purified water of ingredient (9) and mixed to a uniform solution.

(III) Subsequently, the mixture (II) was added to the mixture (I), blended and solubilized to a uniform mixture, followed by coloring with the colour of ingredient (8) to obtain a lotion.

22
EXAMPLE 16

Hand cream:

| (Formula) | |
|---|---|
| (1) Bleached beeswax | 2.0 wt. % |
| (2) Stearic acid | 2.0 |
| (3) Saturated fatty acid (C8–C12) triglyccride | 10.0 |
| (4) Cetyl alcohol | 4.0 |
| (5) Polyethyleneglycol (10EO) monostearate | 2.0 |
| (6) Propyl parahydroxybenzoate | 0.1 |
| (7) Methyl parahydroxybenzoate | 0.1 |
| (8) Triethanolamine | 1.0 |
| (9) Concentrated glycerin | 3.0 |
| (10) Bis.nicotinamide zinc | 0.001 |
| (11) Antioxidant | a sufficient quantity |
| (12) Purified water to make total: | 100.0 |

(Method of preparation)

Ingredients (1) to (12) were blended as described in Example 8 and emulsified. A stable emulsion was obtained.

EXAMPLE 17

Face powder:

| (Formula) | |
|---|---|
| (1) Calcium carbonate, precipitated | 30.0 wt. % |
| (2) Titanium dioxide | 3.0 |
| (3) Zinc stearate | 5.0 |
| (4) Pigment | a sufficient quantity |
| (5) Perfume | a sufficient quantity |
| (6) Compound A | 5.0 |
| (7) Talc to make total: | 100.0 |

(Method of preparation)

Ingredients (1) to (7) were blended to a uniform mixture, and a face powder was prepared according to a method known per se.

EXAMPLE 18

Paste powder:

| (Formula) | |
|---|---|
| (1) Titanium dioxide | 20.0 wt. % |
| (2) Zinc oxide | 5.0 |
| (3) Iron oxide pigment | 5.0 |
| (4) Zinc dipicolinate | 30.0 |
| (5) Perfume | a sufficient quantity |
| (6) Concentrated glycerin | 10.0 |
| (7) Purified water to make total: | 100.0 |

(Method of preparation)

While uniformly blending ingredients (1) to (4), the perfume of ingredient (5) was uniformly sprayed thereto, to which ingredients (6) and (7) were slowly added and kneaded to obtain a paste powder.

EXAMPLE 19

Sunscreen milky lotion:

| (Formula) | |
|---|---|
| (1) Stearic acid | 2.0 wt. % |
| (2) Cetyl alcohol | 1.0 |
| (3) Glyceryl monostearate, self-emulsifying | 1.0 |

-continued

| (Formula) | |
|---|---|
| (4) Dimethylpolysiloxane | 2.0 |
| (5) Cetyl alcohol | 1.0 |
| (6) Dihinokitiolate zinc (II) or Dihinokitiolato zinc (II) | 2.0 |
| (7) Liquid petrolatum | 10.0 |
| (8) Triethanolamine | 1.0 |
| (9) Propylene glycol | 3.0 |
| (10) Titanium oxide | 5.0 |
| (11) Bentonite | 0.5 |
| (12) Bactericides/preservative | a sufficient quantity |
| (13) Perfume | a sufficient quantity |
| (14) Purified water to make total: | 100.0 |

(Method of preparation)

Ingredients (1) to (14) were blended as described in Example 8 and emulsified. A stable emulsion was obtained.

EXAMPLE 20

Lip cream:

| (Formula) | |
|---|---|
| (1) Candelilla wax | 10.0 wt.% |
| (2) Carnauba wax | 4.0 |
| (3) Ceresine | 3.0 |
| (4) Microcrystalline wax | 3.0 |
| (5) Lanolin | 10.0 |
| (6) Glyceryl trioctanoate | 40.0 |

-continued

| (Formula) | |
|---|---|
| (7) Castor oil | 20.0 |
| (8) Zinc dipicolinate | 0.003 |
| (9) Antioxidant | a sufficient quantity |
| (10) Liquid petrolatum to make total: | 100.0 |

(Method of preparation)

Ingredients (1) to (10) were heated (85° C.) to a uniform mixture, defoamed, cast in a mold and rapidly cooled to form a stick-shape product.

EXAMPLE 21

Hydrophilic ointment:

| (Formula) | |
|---|---|
| (1) Stearyl alcohol | 20.0 wt. % |
| (2) White petrolatum | 25.0 |
| (3) Propyl parahydroxybenzoate | 0.2 |
| (4) Methyl parahydroxybenzoate | 0.2 |
| (5) Propylene glycol | 12.0 |
| (6) Compound A | 1.0 |
| (7) Monosodium N-acyl-L-glutamate | 1.0 |
| (8) Purified water to make total: | 100.0 |

(Method of preparation)

Ingredients (1 ) to (8) were blended as described in Example 8 and emulsified. A stable emulsion was obtained.

Examples 22 to 27: (Formula)

TABLE 4

| No. | Ingredients | Example Nos. 22 | 23 | 24 | 25 | 26 | 27 | Comp. Ex. 1 |
|---|---|---|---|---|---|---|---|---|
| 1 | Glyceryl trioctanoate | 30.0 | 30.0 | 30.0 | 30.0 | 30.0 | 30.0 | 30.0 |
| 2 | Bleached beeswax | 2.5 | 2.5 | 2.5 | 2.5 | 2.5 | 2.5 | 2.5 |
| 3 | Glyceryl monostearate, lipophilic | 1.0 | 1.0 | 1.0 | 1.0 | 1.0 | 1.0 | 1.0 |
| 4 | Bathyl stearate | 2.0 | 2.0 | 2.0 | 2.0 | 2.0 | 2.0 | 2.0 |
| 5 | Polyoxyethylene behenyl ether (10EO) | 1.0 | 1.0 | 1.0 | 1.0 | 1.0 | 1.0 | 1.0 |
| 6 | Polyoxyethylene behenyl ether (20EO) | 1.0 | 1.0 | 1.0 | 1.0 | 1.0 | 1.0 | 1.0 |
| 7 | Compound A | 0.093 | — | — | — | — | — | — |
| 8 | Zinc dipicolinate | — | 0.093 | — | — | — | — | — |
| 9 | Dihinokitiolatezinc(II) or Dihinokitiolatozinc(II) | — | — | 0.118 | — | — | — | — |
| 10 | Bis(3,4-dihydroxybenzoate)zinc(II) or Bis(3,4-dihydroxybenzoato)zinc(II) | — | — | — | 0.050 | — | — | — |
| 11 | Bis(L-histidinolate)zinc(II) or Bis(L-histidinolato)zinc(II) | — | — | — | — | 0.066 | — | — |
| 12 | Bis(2,5-pyridinecarboxylato)zinc(II).Na | — | — | — | — | — | 0.132 | — |
| 13 | Purified water | a sufficient quantity | | | | | | |
| | Total | 100.0 wt. % | | | | | | |

(Method of preparation)

(I) Ingredients (1) to (12) were heated to 80° C. and uniformly blended.

(II) Ingredient (13) was heated to 80° C.

(III) Subsequently, (II) was added to the mixture of (I) at 80° C. portionwise, and when smoothly emulsified, the emulsion was cooled to 20° C. with stirring.

Stable emulsions were obtained.

EXAMPLE 28

Emulsion:

| (Formula) | |
|---|---|
| (1) Glyceryl trioctanoate | 30.0 wt. % |
| (2) Bleached beeswax | 2.5 |
| (3) Glyceryl monostearate, lipophilic | 1.0 |
| (4) Batyl stearate | 2.0 |
| (5) Polyoxyethylene behenyl ether (10EO) | 1.0 |
| (6) Polyoxyethylene behenyl ether (20EO) | 1.0 |
| (7) Bactericides/Preservative | a sufficient quantity |

-continued

| (Formula) | |
|---|---|
| (8) Nicotinic acid | 0.1 |
| (9) Zinc chloride | 0.06 |
| (10) Purified water to make total: | 100.0 |

(Method of preparation)

Ingredients (1) to (10) were blended as described in Example 8 and emulsified. A stable emulsion was obtained.

EXAMPLE 29

Emulsion:

| (Formula) | |
|---|---|
| (1) Glyceryl monostearate, lipophilic | 2.5 wt. % |
| (2) Purified avocado oil | 8.0 |
| (3) Hydrogenated lecithin | 1.0 |
| (4) Compound A | 0.1 |
| (5) Bactericides/Preservative | a sufficient quantity |
| (6) Purified water to make total: | 100.0 |

(Method of preparation)

Ingredients (1) to (6) were blended as described in Example 22 and emulsified. A stable emulsion was obtained.

EXAMPLE 30

Lotion:

| (Formula) | |
|---|---|
| (1) 1% NaOH solution | 2.5 wt. % |
| (2) Concentrated glyceril | 1.0 |
| (3) Polyoxyethylene nonylphenyl ether (15EO) | 0.3 |
| (4) Nicotinic acid | 0.1 |
| (5) Zinc chloride | 0.06 |
| (6) Ethyl alcohol | 15.0 |
| (7) Purified water to make total: | 100.0 |

(Method of preparation)

Ingredients (1) to (7) were blended as described in Example 15 and uniformly mixed. A stable lotion was obtained.

EXAMPLE 31

Lotion:

| (Formula) | |
|---|---|
| (1) L-Aspartic acid | 0.1 wt. % |
| (2) Zinc chloride | 0.09 |
| (3) Ethyl alcohol | 5.0 |
| (4) Purified water to make total: | 100.0 |

(Method of preparation)

Ingredients (1) to (4) were blended as described in Example 15 and uniformly mixed. A stable lotion was obtained.

EXAMPLE 32

Two-layered lotion:

| (Formula) | |
|---|---|
| (1) Bis.nicotinamide zinc | 0.3 wt. % |
| (2) Zinc oxide | 0.8 |
| (3) Ethyl alcohol | 5.0 |
| (4) Purified water to make total: | 100.0 |

(Method of preparation)

Ingredients (1) to (4) were blended as described in Example 15 and uniformly mixed to obtain a two-layered lotion.

EXAMPLE 33

Emollient cream:

| (Formula) | |
|---|---|
| (1) Squalane | 5.0 wt. % |
| (2) Octyldodecanol | 6.0 |
| (3) Lanolin, hydrogenated | 2.0 |
| (4) Stearyl alcohol | 7.0 |
| (5) Polyoxyethylene cetyl ether (25EO) | 3.0 |
| (6) Glyceryl monostearate, lipophilic | 2.0 |
| (7) Compound D | 0.5 |
| (8) Concentrated glycerin | 5.0 |
| (9) Preservative | a sufficient quantity |
| (10) Purified water to make total: | 100.0 |

(Method of preparation)

Ingredients (1) to (10) were blended as described in Example 8 to obtain an emollient cream by a method known per se.

EXAMPLE 34

Sunscreen cream:

| (Formula) | |
|---|---|
| (1) Solid paraffin | 5.0 wt. % |
| (2) Bleached beeswax | 10.0 |
| (3) Microcrystalline wax | 5.0 |
| (4) White petrolatum | 10.0 |
| (5) Squalane | 40.0 |
| (6) Polyoxyethylene sorbitan monolaurate (20EO) | 1.0 |
| (7) Sorbitan sesquioleate | 5.0 |
| (8) Nicotinamide | 0.1 |
| (9) Zinc chloride | 0.05 |
| (10) pH control agents | a sufficient quantity |
| (11) Preservative | a sufficient quantity |
| (12) Purified water to make total: | 100.0 |

(Method of preparation)

Ingredients (1) to (12) were blended as described in Example 8 to obtain a sunscreen cream by a method known per se.

EXAMPLE 35

Lotion:

| (Formula) | |
|---|---|
| (1) Concentrated glycerin | 5.0 wt. % |
| (2) Polyethylene glycol 1500 | 2.0 |
| (3) Polyoxyethylene oleylether (15EO) | 2.0 |
| (4) Compound C | 1.5 |

-continued

| (Formula) | |
|---|---|
| (5) Ethanol | 8.5 |
| (6) Preservative | a sufficient quantity |
| (7) Purified water to make total: | 100.0 |

(Method of preparation)

Ingredients (1) to (7) were blended as described in Example 15 to obtain a lotion by a method known per se.

EXAMPLE 36

Hairtonic:

| (Formula) | |
|---|---|
| (1) Ethanol | 70.0 wt. % |
| (2) dl-α-Tocopheryl acetate | 0.05 |
| (3) Pantothenylalcohol | 0.2 |
| (4) Propylene glycol | 3.0 |
| (5) Ethanol-soluble polypeptide | 8.5 |
| (6) Compound B | 0.1 |
| (7) pH control agents | a sufficient quantity |
| (8) Perfume | a sufficient quantity |
| (9) Preservative | a sufficient quantity |
| (10) Purified water to make total: | 100.0 |

(Method of preparation)

Ingredients (1) to (10) were blended as described in Example 15 to obtain a hair tonic by a method known per se.

EXAMPLE 37

(Effect of a composition with zinc compound one the UV-induced skin damage):

As a light source of UV irradiation, two FL20SE health care fluorescent lamps (Toshiba) were used.

The degree of UV-induced skin damage was evaluated by the number of sunburn cells (SBC, sunburn cell; cells which have been damaged by UV irradiation) in the epidermis after UV irradiation.

The compositions used here were those prepared in the examples 22, 24, 25, 26 and 27.

Hairless mice (BALB/c Jcr-hr, Nihon Crea Co.) were used and the back hair was shaved. The formulation of Example 1 was used as a base of the composition. Untreated mice were used as negative control.

These compositions were applied 3 times every 8 hours to the mice skin under the anesthesia. Twenty-four hours after the last application, the UV light was irradiated to the trunk of each mouse at a dose of 250 mJ/cm$^2$. Twenty four hours after irradiation the mice were sacrificed, and the skin was excised. The skin specimens were fixed with 10% formalin. After cutting by the routine method, each skin section was stained with hematoxylin and eosin. The number of SBCs of the epidermis was examined by three individuals. The mean value of the three data was adopted.

The results are shown in Table 5.

TABLE 5

| Treatment with | Number of SBC ( /mm) | Mean |
|---|---|---|
| Base (Example 1) | 4.2, 6.0, 3.0 | 4.4 |
| Example 22 | 1.8, 0.6, 1.2 | 1.2 |
| Example 24 | 1.2, 2.4, 1.2 | 1.6 |
| Example 25 | 1.2, 1.2, 3.6 | 2.0 |
| Example 26 | 0.6, 2.4, 1.2 | 1.4 |
| Example 27 | 3.0, 3.0, 4.8 | 3.6 |
| Control | 8.4, 3.0, 3.0 | 4.8 |

From the data of Table 5, it was confirmed that each of the sample compositions reduced the UV-induced skin damage more effectively than Comparative Example 1 or control.

From these results, it is suggested that each of sample compositions is useful as an agent for treating the skin diseases and radiation-induced damage or as a cosmetic component for preventing the sunburn and ameliorating the dermatitis caused by UV light.

EXAMPLE 38

(Effect of a composition with a zinc compound on the UVB-induced erythema):

As a light source of UV irradiation, DERMARAY-100 (Clinical Supply) equipped with FL20SE-30 sunlamp tubes (Toshiba) was used.

The degree of erythema was examined using Derma Spectrometer (trademark).

Two Hartley guinea pigs (body weight: 300 g, obtained from Nihon Crea Co.) were used and their back hair was shaved with an electric hair clipper and an electric shaver. Their back skin was applied with compositions of Examples 22 and 23 (1.0 cm$^2$). A composition Comparative Example 1 was used as a control. Twenty-four hours after the application, the compositions were removed from the skin, and the skin was irradiated with UVB at a dose of 3 MED (900 mJ/cm$^2$).

The time course of erythema was measured from 0 to 72 hours after UV irradiation under unanesthesia. The degree of erythema was presented as an erythema index. Detailed information about the erythema index was available by the report of Diffey ["Brit. J. Dermatol. Diffey, B. L., et al., 111, 663–672 (1984)]. The erythema index is calculated by the following formula:

$$\text{Erythema Index} = \text{Log}_{10} \frac{\text{absorbance of the reflected red light}}{\text{absorbance of the reflected green light}}$$

Figure 4:
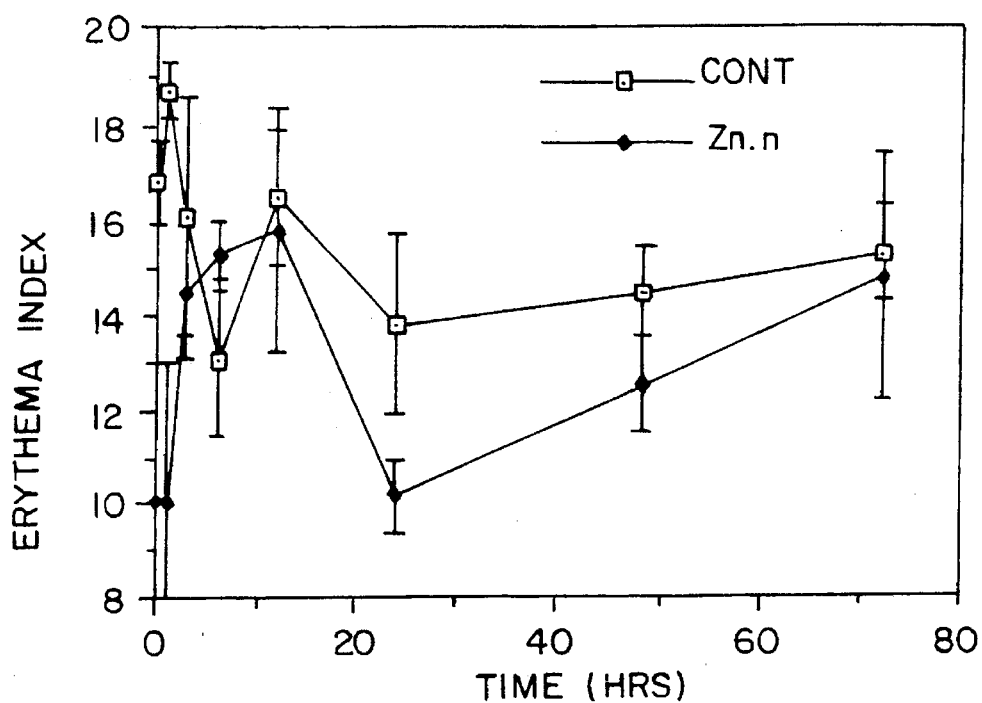
FIG. 4 is a chart showing the effect of the composition of Example 22 on the erythema caused by the UV rays as described in Example 34.
Figure 5:
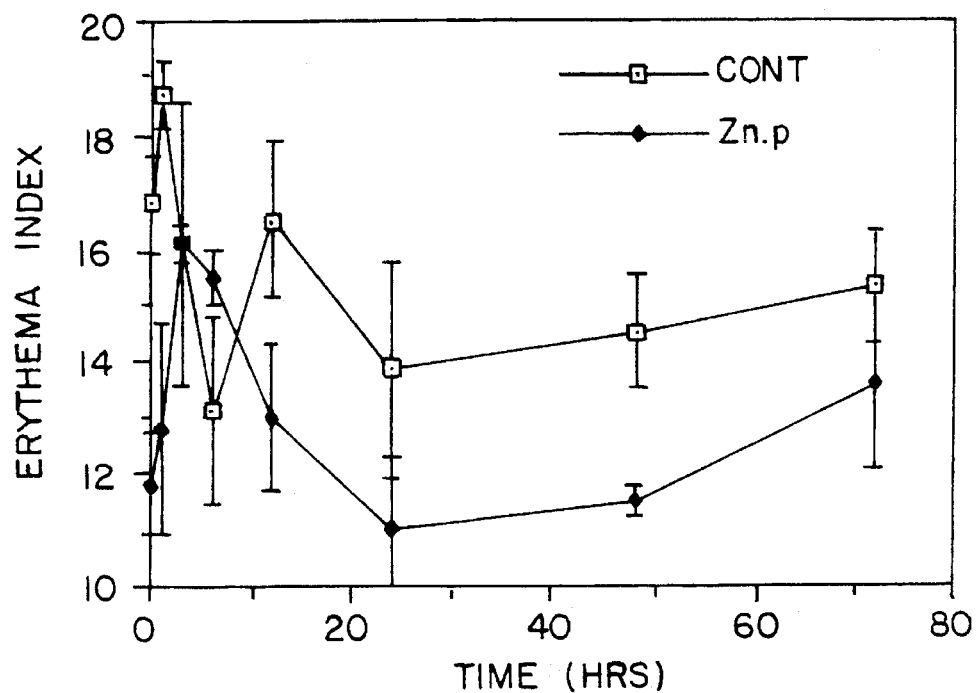
FIG. 5 is a chart showing the effect of the composition of Example 23 on the erythema caused by the UV rays as described in Example 34.

The results are shown in FIGS. 4 and 5. In FIG. 4, the Y axis of ordinate shows the erythema index, and the X axis of abscissa shows the time course after UV irradiation. In addition, "cont" indicates a control group, and "Zn.n" indicates data of Example 22. In FIG. 5, the Y axis of ordinate shows the erythema index, and the X axis of abscissa shows the time course after UV irradiation. In addition, "cont" indicates a control group, and "Zn.p" indicates data of Example 23.

From the results of FIGS. 4 and 5, it was obvious that compared with control, both compositions of Example 22 and 23 suppressed not only immediate-type erythema but also delayed-type erythema after 24 hours of UV irradiation.

Generally, the time course of UV induced erythema shows two peaks, one is the erythema which appears immediately after UV irradiation, and another is the delayed-type erythema which appears about 24 hours after UV irradiation. As described above, the compositions with a zinc compounds, which are made possible by the present invention, suppress the UV-induced erythema. Therefore, they are useful for ameliorating and preventing the UV-induced dermatitis and sunburn.

EXAMPLE 39

(Effect of topical application of zinc compound on the induction of MT and suppression of the SBC formation):

Using hairless mice [BALB/c Jcl-hr, obtained from Nihon Crea, age: 7 weeks old], we examined the MT inducing effect and suppressing effect of SBC formation by the zinc compounds. Each group of hairless mice consisted of 3 mice.

Both zinc compounds of B and C were dissolved in 1.5% ethanol solution and adjusted to $3\times10^{-3}$M and $3\times10^{-4}$M. In this experiment, 1.5% ethanol solution was used as a control.

Under general anesthesia with chloral hydrate (3.6%) by intraperitoneal injection (0.8 cc/100 g body weight), the zinc compounds or ethanol solution topically applied three times to the back and ear of the mice every 8 hours.

The excised skin specimens were fixed with formalin, and the reactivity with the MT antibody was examined by the same method as described in Example 1.

The results are shown in Table 6. In the table, (−) indicates no reactivity with MT, (+) indicates a weak reactivity, (++) indicates a moderate reactivity and (+++) indicates a strong reactivity.

TABLE 6

| | Control Group | | Compound B | | | | Compound C | | | |
| | | | $3 \times 10^{-4}$M | | $3 \times 10^{-3}$M | | $3 \times 10^{-4}$M | | $3 \times 10^{-3}$ | |
| | Epidermis | Sebaceous glands | Epidermis | Sebaceous glands | Epidermis | Sebaceous glands | Epidermis | Sebaceous glands | Epidermis | Sebaceous glands |
|---|---|---|---|---|---|---|---|---|---|---|
| Ear | − | + | + | + | ++ | ++ | − | ++ | + | + |
| | + | − | | | + | ++ | | | + | + |
| | − | + | | | | | | | | |
| Back | + | + | + | ++ | + | +++ | + | ++ | ++ | + |
| | − | + | | | ++ | ++ | | | ++ | ++ |
| | + | + | | | | | | | | |

As was shown in Table 6, the MT inducing effect was scarcely observed in the control group, in contrast in the zinc compound-applied groups, more intense MT induction was observed in the epidermis and sebaceous glands, as the concentration dependent manner.

On the other hand, after topical application of the zinc compounds three times every 8 hours, the back and ear skin of the mice were irradiated with UVB at dose of 200 mJ/cm$^2$.

Twenty four hours after UVB irradiation, the mice were sacrificed, and the skin of back and ear were obtained using a 6 mm trepan. The excised skin was fixed with 10% formalin, and skin sections were prepared. Each sample was stained with hematoxylin and eosin, and then the number of SBCs in the skin sections was counted per 1 mm. The results are shown in Table 7.

TABLE 7

| Treatment with | Number of SBC ( /mm) | Mean |
|---|---|---|
| Control | 4.3, 6.3, 3.2 | 4.6 |
| Compound C | 4.8, 4.2, 3.4 | 4.1 |
| Compound B | 4.2, 2.3, 3.3 | 3.3 | of SBCs of the zinc-compound applied-groups was less than that of the control group. This indicates that the zinc compounds suppress the UV-induced cell damage.

Industrial Applicability

The present inventions have an excellent character as therapeutic agents for skin diseases, MT inducers, suppressing agents of SBC formation, and cosmetic compositions for screening the UV light. These agent are effective to sunburn, various skin diseases, and radiation induced damage.

Considering these findings, the present inventions which have the characters as the therapeutic agents for skin diseases, SBC production suppressing agents were useful in the treatment of skin diseases such as dermatitis, sunburn, neurodermatitis, cutaneous vasculitis, psoriasis, erythema multiforme, Beh et disease, varicella dermatosis, cement dermatitis, eczema and anogenital pruritus. These agents are also useful in the treatment of radiation-induced symptom such as leukopenia, alopecia, erythema, nausea, anorexia and general fatigue. In addition, the compositions of the present invention are useful for preventing sunburn and aging of the skin. Furthermore, the absorption of zinc compounds is very good by oral administration and by topical application. These agents are long acting and do not exhibit any serious toxicity.

We claim:

1. A method of suppressing the production of sunburn cells, which comprises administering an effective amount of a composition comprising, as an effective component, a zinc salt, a zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

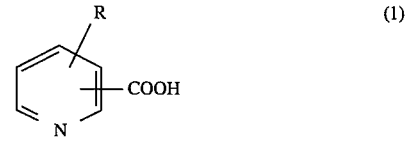

wherein R represents hydrogen, hydroxy, nitro, halogen, alkoxy, alkyl, carboxy, —COOM, wherein M represents an alkali metal, or an oxide on a nitrogen atom.

2. The method according to claim 1, wherein the effective component is a zinc salt, a zinc complex or a salt thereof of a compound selected from the group consisting of nicotinamides, picolinamides, hinokitiols and pyridine carboxylic acids represented by formula (1) wherein R is hydrogen, carboxy or —COOM wherein (M represents an alkali metal).

3. The method according to claim 1, wherein the effective component is a zinc salt, a zinc complex or a salt thereof of 3-pyridine carboxylic acid.

4. The method according to claim 1, wherein the effective component is a zinc salt, a zinc complex or a salt thereof of nicotinamide or picolinamide.

5. The method according to claim 1, wherein the effective component is a zinc salt, a zinc complex or a salt thereof of a D-, L- or DL- amino acids selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

6. The method according to claim 1, wherein the effective component is a zinc salt, zinc complex or a salt thereof of a polypeptide having a molecular weight of 3000 or less and composed of the same or different 2–10 amino acids selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

7. The method according to claim 1, wherein the effective component is a zinc salt, a zinc complex or a salt thereof of a polypeptide having a molecular weight of 3000 or less and including histidine in the amino acid sequence.

8. The method according to claim 1, wherein the effective component is a zinc salt, a zinc complex or a salt thereof of a polypeptide selected from the group consisting of di L-arginine-L-aspartic acid, L-arginine-L-glutamic acid, glycylglycine, L-glutamic acid-DL-alanine, di DL-pyrrolidone carboxylic acid, L-alanyl-glycyl-glycine, β-alanyl-L-histidine, glycyl-glycyl-glycine, glycyl-glycyl-glycyl-glycine, L-leucyl-glycyl-glycine, DL-leucyl-glycyl-DL-phenylalanine and glutathione.

9. The method according to claim 1, wherein the effective component is zinc dipicolinate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na.

10. A method of inducing metallothionein which comprises administering an effective amount of a composition comprising, as an effective component, a zinc salt, a zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

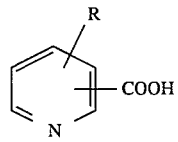

wherein R represents hydrogen, hydroxy, nitro, halogen, alkoxy, alkyl, carboxy, —COOM, M represents an alkali metal, or an oxide on a nitrogen atom.

11. The method according to claim 10, wherein the effective component is a zinc salt, a zinc complex or a salt thereof of a compound selected from the group consisting of nicotinamides, picolinamides, hinokitiols and pyridine carboxylic acids represented by formula (1) wherein R is hydrogen, carboxy or —COOM, wherein M represents an alkali metal.

12. The method according to claim 10, wherein the effective component is a zinc salt, a zinc complex or a salt thereof of 3-pyridine carboxylic acid, nicotinamide or picolinamide, zinc dipicolate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

13. The method according to claim 10, wherein the effective component is a zinc salt, a zinc complex or a salt thereof of a polypeptide having a molecular weight of 3000 or less and composed of the same or different 2–10 amino acids a of D-, L- or DL- type selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

14. The method according to claim 10, wherein the effective component is zinc dipicolinate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

15. A method of treating a skin disease which comprises administering an effective amount of a composition comprising, as an effective component, a zinc salt, zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

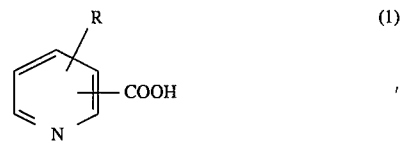

wherein R represents hydrogen, hydroxy, nitro, halogen, alkoxy, alkyl, carboxy, —COOM, wherein M represents an alkali metal or an oxide on a nitrogen atom.

16. The method according to claim 15, wherein the skin disease is selected from the group consisting of dermatitis, sunburn, neurodermatitis, eczema, anogenital pruritus, psoriasis, erythema multiforme, dermatoangiopathy, Beh et disease, varicella dermatosis and cement dermatitis.

17. The method according to claim 15, wherein the effective component is a zinc salt, zinc complex or a salt thereof of a compound selected from the group consisting of nicotinamides, picolinamides, hinokitiols and pyridine carboxylic acids represented by formula (1) wherein R is hydrogen, carboxy or —COOM, wherein M represents an alkali metal.

18. The method according to claim 15, wherein the effective component is a zinc salt, zinc complex or a salt thereof of 3-pyridine carboxylic acid, nicotinamide or picolinamide, zinc dipicolate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

19. The method according to claim 15, wherein the effective component is a zinc salt, zinc complex or a salt thereof of a polypeptide having a molecular weight of 3000 or less and composed of the same or different 2–10 amino acids of a D-, L- or DL- type selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

20. The method according to claim 15, wherein the effective component is zinc dipicolinate, dihinokitiolate zinc or dihinokitiolato zinc, bis(L-histidinolate)zinc(II), or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

21. A cosmetic composition which comprises, as an effective component, a zinc salt, a zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

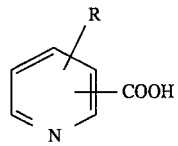

wherein R represents hydrogen, hydroxy, nitro, halogen, alkoxy, alkyl, carboxy, —COOM, wherein M represents an alkali metal, or an oxide on a nitrogen atom, and a carrier.

22. The composition according to claim 21, wherein the effective component is a zinc salt, zinc complex or a salt thereof of a compound selected from the group consisting of nicotinamides, picolinamides, hinokitiols and pyridine carboxylic acids represented by formula (1) wherein R is hydrogen, carboxy or —COOM, wherein M represents an alkali metal.

23. The composition according to claim 21, wherein the effective component is a zinc salt, zinc complex or a salt thereof of 3-pyridine carboxylic acid.

24. The composition according to claim 21, wherein the effective component is a zinc salt, zinc complex or a salt thereof of nicotinamide or picolinamide.

25. The composition according to claim 21, wherein the effective component is a zinc salt, zinc complex or a salt thereof of a D-, L- or DL- type amino acid selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

26. The composition according to claim 21, wherein the effective component is a zinc salt, zinc complex or a salt thereof of a polypeptide having a molecular weight of 3000 or less and composed of the same or different 2–10 amino acids of a D-, L- or DL- type selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

27. The composition according to claim 21, wherein an effective component is a zinc salt, zinc complex or a salt thereof of a polypeptide having a molecular weight of 3000 or less and including histidine in the amino acid sequence thereof.

28. The composition according to claim 21, wherein the effective component is a zinc salt, zinc complex or a salt thereof of a polypeptide selected from the group consisting of di L-arginine-L-aspartic acid, L-arginine-L-glutamic acid, glycylglycine, L-glutamic acid-DL-alanine, di DL-pyrrolidone carboxylic acid, L-alanyl-glycyl-glycine, β-alanyl-L-histidine, glycyl-glycyl-glycine, glycyl-glycyl-glycyl-glycine, L-leucyl-glycyl-glycine, DL-leucyl-glycyl-DL-phenylalanine and glutathione.

29. The composition according to claim 21, wherein the effective component is zinc dipicolinate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

30. An ultraviolet ray screening cosmetic composition which comprises, as an effective component, a zinc salt, a zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

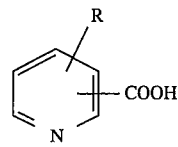

wherein R represents hydrogen, hydroxy, nitro, halogen, alkoxy, alkyl, carboxy, —COOM, wherein M represents an alkali metal or an oxide on a nitrogen atom, and a cosmetic base;
wherein said effective component is present in an amount sufficient to suppress the production of sunburn cells or to screen ultraviolet rays.

31. The ultraviolet ray screening cosmetic composition according to claim 30, wherein the effective component is a a zinc salt, zinc complex or a salt thereof of a compound selected from the group consisting of nicotinamides, picolinamides, hinokitiols and pyridine carboxylic acids represented by formula (1) wherein R is hydrogen, carboxy or —COOM, wherein M represents an alkali metal.

32. The ultraviolet ray screening cosmetic composition according to claim 30, wherein the effective component is a zinc salt, a zinc complex or a salt thereof of 3-pyridine carboxylic acid.

33. The ultraviolet ray screening cosmetic composition according to claim 30, wherein the effective component is a zinc salt, a zinc complex or a salt thereof of nicotinamide or picolinamide.

34. The ultraviolet ray screening cosmetic composition according to claim 30, wherein the effective component is a zinc salt, a zinc complex or a salt thereof of a D-, L- or DL-type amino acid selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

35. The ultraviolet ray screening cosmetic composition according to claim 30, wherein the effective component is a zinc salt, a zinc complex or a salt thereof of a polypeptide having a molecular weight of 3000 or less and composed of the same or different 2–10 amino acids of D-, L- or DL- type selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

36. The ultraviolet ray screening cosmetic composition according to claim 30, wherein the effective component is a zinc salt, a zinc complex or a salt thereof of a polypeptide having a molecular weight of 3000 or less and including histidine in the amino acid sequence thereof.

37. The ultraviolet ray screening cosmetic composition according to claim 30, wherein the effective component is a zinc salt, a zinc complex or a salt thereof of a polypeptide selected from the group consisting of di L-arginine-L-aspartic acid, L-arginine-L-glutamic acid, glycylglycine, L-glutamic acid-DL-alanine, di DL-pyrrolidone carboxylic acid, L-alanyl-glycyl-glycine, β-alanyl-L-histidine, glycyl-glycyl-glycine, glycyl-glycyl-glycyl-glycine, L-leucyl-glycyl-glycine, DL-leucyl-glycyl-DL-phenylalanine and glutathione.

38. The ultraviolet ray screening cosmetic composition according to claim 30, wherein the effective component is zinc dipicolinate, dihinokitiolate zinc or dihinokitiolato zinc, bis(L-histidinolate)zinc(II) or bis(L-histidinolato)zinc(II), bis(3,4-dihydroxybenzoate)zinc(II) or bis(3,4-dihydroxybezoato)zinc(II), or bis(2,5-pyridine carboxylate)zinc(II).2Na or bis(2,5-pyridine carboxylato)zinc(II).2Na.

39. A method of screening ultraviolet rays which comprises administering an effective amount of a cosmetic composition comprising, as an effective component, a zinc salt, zinc complex or a salt thereof of a compound selected from the group consisting of nicotinamides, picolinamides, 3,4-dihydroxybenzoic acids, amino acids, peptides, hinokitiols and pyridine carboxylic acids represented by the following formula (1):

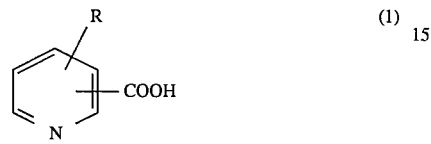

wherein R represents hydrogen, hydroxy, nitro, halogen, alkoxy, alkyl, carboxy, —COOM, wherein M represents an alkali metal or an oxide on a nitrogen atom.

40. The method according to claim 39, wherein the effective component is a zinc a salt, zinc complex or a salt thereof of a compound selected from the group consisting of nicotinamides, picolinamides, hinokitiols and pyridine carboxylic acids represented by formula (1) wherein R is hydrogen, carboxy or —COOM, wherein M represents an alkali metal.

41. The method according to claim 39, wherein the effective component is a zinc salt, a zinc complex or a salt thereof of 3-pyridine carboxylic acid.

42. The method according to claim 39, wherein the effective component is a zinc salt, a zinc complex or a salt thereof of nicotinamides and picolinamides.

43. The method according to claim 39, wherein the effective component is a zinc salt, a zinc complex or a salt thereof of a D-, L- or DL-type amino acid selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

44. The method according to claim 39, wherein the effective component is a zinc salt, a zinc complex or a salt thereof of a polypeptide having a molecular weight of 3000 or less and composed of the same or different 2–10 amino acids of a D-, L- or DL- type selected from the group consisting of glycine, alanine, serine, cysteine, djenkolic acid, aminobutyric acid, threonine, valine, methionine, leucine, isoleucine, phenylalanine, tyrosine, thyroxine, proline, tryptophan, taurine, aspartic acid, glutamic acid, arginine, lysine, ornithine, and histidine.

45. The method according to claim 39, wherein the effective component is a zinc salt, a zinc complex or a salt thereof of a polypeptide having a molecular weight of 3000 or less and including histidine in the amino acid sequence thereof.

46. The method according to claim 39, wherein the effective component is a zinc salt, a zinc complex or a salt thereof of a polypeptide selected from the group consisting of di L-arginine-L-aspartic acid, L-arginine-L-glutamic acid, glycylglycine, L-glutamic acid-DL-alanine, di DL-pyrrolidone carboxylic acid, L-alanyl-glycyl-glycine, β-alanyl-L-histidine, glycyl-glycyl-glycine, glycyl-glycyl-glycyl-glycine, L-leucyl-glycyl-glycine, DL-leucyl-glycyl-DL-phenylalanine and glutathione.

47. The method according to claim 39, wherein the effective component is zinc dipicolinate, dihinokitiolate zinc or dihinokitiolato zinc, bis(L-histidinolate)zinc(II), or bis(L-histidinolato)zinc(II), bis(3,4-dihydroxybenzoate)zinc(II) or bis(3,4-dihydroxybenzoato)zinc(II), or bis(2,5-pyridine carboxylate)zinc(II).2Na or bis(2,5-pyridine carboxylato)zinc(II).2Na.

48. A compound between nicotinic acid and zinc that has the following physical properties:

Crystal form: White powder or white plates

Elemental analysis (%):
C 45.60
H 2.83
N 8.92
Zn 21.16

NMR spectrum:
Solid $^{13}$C-NMR δ ppm; 172.5 (C=O)
150.1 (C-6,2)
139.7 (C-4)
132.5 (C-3)
125.5 (C-5)

| IR spectrum: | |
| --- | --- |
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage.

49. A method of suppressing the production of sunburn cells, which comprises administering an effective amount of a composition containing a compound between nicotinic acid and zinc that has the following physical properties:

Crystal form: White powder or white plates

Elemental analysis (%):
C 45.60
H 2.83
N 8.92
Zn 21.16

NMR spectrum:
Solid $^{13}$C-NMR δ ppm; 172.5 (C=O)
150.1 (C-6,2)
139.7 (C-4)
132.5 (C-3)
125.5 (C-5)

| IR spectrum: | |
| --- | --- |
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage.

50. A method of inducing metallothionein, which comprises administering an effective amount of a composition containing a compound between nicotinic acid and zinc that has the following physical properties:

Crystal form: White powder or white plates

Elemental analysis (%):
C 45.60
H 2.83

N 8.92
Zn 21.16
NMR spectrum:
  Solid $^{13}$C-NMR δ ppm; 172.5 (C=O)
    150.1 (C-6,2)
    139.7 (C-4)
    132.5 (C-3)
    125.5 (C-5)

| IR spectrum: | |
|---|---|
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage.

51. A treatment method for a skin disease, which comprises administering an effective amount of a composition containing a compound between nicotinic acid and zinc that has the following physical properties:
  Crystal form: White powder or white plates
  Elemental analysis (%):
    C 45.60
    H 2.83
    N 8.92
    Zn 21.16
  NMR spectrum:
    Solid $^{13}$C-NMR δ ppm; 172.5 (C=O)
      150.1 (C-6,2)
      139.7 (C-4)
      132.5 (C-3)
      125.5 (C-5)

| IR spectrum: | |
|---|---|
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage.

52. A treatment method according to claim 51, wherein the skin disease is selected from the group consisting of dermatitis, sunburn, neurodermatitis, eczema, anogenital pruritus, psoriasis, erythema multiforme, dermatoangiopathy, Beh et disease, varicella dermatosis and cement dermatitis.

53. A cosmetic composition comprising a compound as defined in claim 48 and a cosmetic base.

54. An ultraviolet ray screening cosmetic composition comprising a compound between nicotinic acid and zinc that has the following physical properties:
  Crystal form: White powder or white plates
  Elemental analysis (%):
    C 45.60
    H 2.83
    N 8.92
    Zn 21.16
  NMR spectrum:
    Solid $^{13}$C-NMR δ ppm; 172.5 (C=O)
      150.1 (C-6,2)
      139.7 (C-4)
      132.5 (C-3)
      125.5 (C-5)

| IR spectrum: | |
|---|---|
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage, and a cosmetic base suitable for an ultraviolet ray screening composition;
wherein said effective component is present in an amount sufficient to screen ultraviolet rays.

55. A method of screening ultraviolet rays which comprises administering an effective amount of a cosmetic composition containing a compound between nicotinic acid and zinc that has the following physical properties:
  Crystal form: White powder or white plates
  Elemental analysis (%):
    C 45.60
    H 2.83
    N 8.92
    Zn 21.16
  NMR spectrum:
    Solid $^{13}$C-NMR δ ppm; 172.5 (C=O)
      150.1 (C-6,2)
      139.7 (C-4)
      132.5 (C-3)
      125.5 (C-5)

| IR spectrum: | |
|---|---|
| 2700–3600 cm$^{-1}$ | m (O—H stretching vibration) |
| 1638 (1600–1650) | s (COO$^-$, anion of carboxylic acid, antisymmetric vibration) |
| 1416 (1360–1450) | s (COO$^-$, anion of carboxylic acid, symmetric vibration), | having a peak in the vicinity of 220 cm$^{-1}$, which indicates a Zn-N linkage.

56. The method according to claim 1, wherein the effective component is a dihinokitiolate zinc or dihinokitiolato zinc.

57. The ultraviolet ray screening cosmetic composition according to claim 30, wherein the effective component is a dihinokitiolate zinc or dihinokitiolato zinc.

58. The method according to claim 39, wherein the effective component is a dihinokitiolate zinc or dihinokitiolato zinc.

\* \* \* \* \*